United States Patent
Riker et al.

(10) Patent No.: US 7,831,289 B2
(45) Date of Patent: Nov. 9, 2010

(54) PLANNING SYSTEM, METHOD AND APPARATUS FOR CONFORMAL RADIATION THERAPY

(75) Inventors: Robert Riker, Sewickley, PA (US); Merle Romesberg, III, Pittsburgh, PA (US)

(73) Assignee: Best Medical International, Inc., Springfield, VA (US)

( * ) Notice: Subject to any disclaimer, the term of this patent is extended or adjusted under 35 U.S.C. 154(b) by 1287 days.

(21) Appl. No.: 10/960,424

(22) Filed: Oct. 7, 2004

(65) Prior Publication Data

US 2005/0111621 A1     May 26, 2005

Related U.S. Application Data

(60) Provisional application No. 60/518,020, filed on Oct. 7, 2003.

(51) Int. Cl.
*A61B 5/05*     (2006.01)
(52) U.S. Cl. ............ 600/407; 378/65; 600/427
(58) Field of Classification Search .......... 378/65; 600/407, 427
See application file for complete search history.

(56) References Cited

U.S. PATENT DOCUMENTS

| | | | |
|---|---|---|---|
| 3,861,807 A | | 1/1975 | Lescrenier et al. |
| 3,987,281 A | * | 10/1976 | Hodes .......... 600/407 |
| 4,455,609 A | | 6/1984 | Inamura et al. |
| 5,373,844 A | * | 12/1994 | Smith et al. ........ 600/427 |
| 5,511,549 A | * | 4/1996 | Legg et al. ........ 600/436 |
| 5,596,619 A | | 1/1997 | Carol |
| 6,038,283 A | | 3/2000 | Carol et al. |
| 6,222,544 B1 | * | 4/2001 | Tarr et al. ........ 715/839 |
| 6,360,116 B1 | * | 3/2002 | Jackson et al. ........ 600/427 |
| 6,393,096 B1 | | 5/2002 | Carol et al. |
| 6,435,717 B1 | | 8/2002 | Koehler et al. |

(Continued)

FOREIGN PATENT DOCUMENTS

EP     0911065 A3     4/1999

(Continued)

OTHER PUBLICATIONS

M Romesberg, "Novel Application of Serial Tomotherapy Based Intensity Modulated Radiation Therapy to a Cobalt (60Co) Teletherapy System", Med. Phys. 34, 2474 (2007) (Abstract).

(Continued)

*Primary Examiner*—Long V Le
*Assistant Examiner*—Ellsworth Weatherby

(57) ABSTRACT

A system and associated methods to determine an optimal radiation beam arrangement are provided. The system includes a computer planning apparatus which includes a treatment plan optimization computer having a memory and an input device in communication with the treatment plan optimization computer to provide user access to control functions of plan optimization software. An image gathering device is in communication with the treatment plan optimization computer through a communications network to provide an image slice of the tumor target volume and the non-target structure volume. The plan optimization software computationally obtains and then optimizes a proposed radiation beam arrangement iteratively based on constraints to form an optimized radiation beam arrangement. A conformal radiation therapy delivery device in communication with the treatment plan optimization computer through the communications network then applies the optimized radiation beam arrangement to the patient.

38 Claims, 17 Drawing Sheets

U.S. PATENT DOCUMENTS

| | | | |
|---|---|---|---|
| 6,560,311 B1 * | 5/2003 | Shepard et al. | 378/65 |
| 2002/0080915 A1 | 6/2002 | Frohlich | |
| 2002/0122530 A1 | 9/2002 | Erbel et al. | |
| 2004/0138556 A1 | 7/2004 | Cosman | |

FOREIGN PATENT DOCUMENTS

| | | |
|---|---|---|
| EP | 1041918 | 11/2000 |
| WO | WO 02/49044 | 6/2002 |
| WO | WO 02/49044 A2 | 6/2002 |

OTHER PUBLICATIONS

M Romesberg, R Pino, R Rubin, J Denisi, P Nizin, "A Novel, Heterogeneity Inclusive, Pencil-Beam Based Algorithm to Improve Lung IMRT Using the Corvus Planning System", Med. Phys. 33, 2286 (2006) (Abstract).

D. Wang, R. Hill, S. Lam, M. Romesberg, "Implementation of a Pseudo-IMAT Technique In An Inverse IMRT Planning System." American Association of Physicists in Medicine 2003 Works in Progress (Abstract).

M Romesberg, R Riker, R Hill, J Denisi, and D Spellman, "Real-Time Isodose Sculpting, CDVH Manipulation, and Delivery Efficiency Control in IMRT", Med. Phys. 32, 1896 (2005).

M. Romesberg, J. Bartels, "Controlling the tradeoff between delivery efficiency and dosimetric fitness in IMRT." American Association of Physlcists in Medicine 2002 Works in Progress.

M. Romesberg, J. Bartels, "Controlling the tradeoff between delivery efficiency and dosimetric fitness in IMRT." Abstract 2002.

M. Romesberg, S. Zasadil, R. Hill, W. Tomer, "Comparing Algorithms for Optimizing Monitor Unit Settings along with Pencil Beam Intensities in IMRT." AAPM 2001 Works in Progress.

C. Nikou, B. Jaramaz, A. DiGioia, M. Blackwell, M. Romesberg, M. Green, "POP: Preoperative Planning and Simulation Software for Total Hip Replacement Surgery." MICCAI 1999: 868-875.

M. Romesberg, J. Bartels, B. Curran, R. Hill, R. Nash, "A Comparison of Simulated Annealing and Gradient Descent Optimization Algorithms in IMRT." Radiological Society of North America 2002 Scientific Papers.

M. Romesberg, "A Novel Heterogeneity Inclusive, Pencil Beam Based Algorithm to Improve Lung IMRT Using the CORVUS Planning System"; Nomos Radiation Oncology, AAPM meeting 2006.

M. Romesberg, "Novel Application of Serial Tomotherapy Based Intensity Modulated Radiation Therapy to a Cobalt (60CO) Teletherapy System," AAPM Meeting 2005.

M. Romesberg, "Real-Times Isodose Sculpting, CDVH Manipulation, and Delivery Efficiency Control in IMRT," AAPM Meeting 2005.

Nomos Corporation, Peacock Plan 1.12 User Manual 1996.

* cited by examiner

FIG. 9

| PTV CONSTRAINTS | | | | |
|---|---|---|---|---|
| USE | NAME | | MIN (GY) | MAX (GY) |
| ✓ | PROSTATE - TARGET | | 69.0 | 82.6 |
| ✓ | SEMINAL VESICLES - TARGET | | 69.0 | 81.4 |
| ✓ | NORMAL TISSUE | | | 82.6 |
| ✓ | BLADDER | | | 81.0 |
| ✓ | RECTUM | | | 80.1 |

FIG. 10

| STRUCTURE NAME | LIMIT (GY) | VOL ABOVE LIMIT (%) | MIN (GY) | MAX (GY) | MEAN (GY) |
|---|---|---|---|---|---|
| TISSUE | 75.60 | | | | |
| NON-TARGET TISSUE | 75.60 | | | 82.72 | |
| BLADDER | 65.00 | 19.88 | 6.00 | 80.52 | 40.67 |
| RECTUM | 65.00 | 22.68 | 6.71 | 79.07 | 46.51 |

PLANNING SYSTEM, METHOD AND APPARATUS FOR CONFORMAL RADIATION THERAPY

RELATED APPLICATIONS

This application claims the benefit under 35 U.S.C. §119(e) of U.S. Provisional Application Ser. No. 60/518,020, filed Oct. 7, 2003, titled "Planning System, Method, and Apparatus for Conformal Radiation Therapy," which is incorporated by reference in its entirety.

BACKGROUND OF THE INVENTION

1. Field of the Invention

The present invention relates generally to radiation therapy, and more specifically to conformal radiation therapy of tumors, and particularly to a radiation therapy treatment planning system, methods, and apparatus for conformal radiation therapy.

2. Description of Related Art

Modern day radiation therapy of tumors has two goals: eradication of the tumor, and avoidance of damage to healthy tissue and organs present near the tumor. It is known that a vast majority of tumors can be eradicated completely if a sufficient radiation dose is delivered to the tumor volume; however, complications may result from use of the necessary effective radiation dose, due to damage to healthy tissue which surrounds the tumor, or to other healthy body organs located close to the tumor. The goal of conformal radiation therapy is to confine the delivered radiation dose to only the tumor volume defined by the outer surfaces of the tumor, while minimizing the dose of radiation to surrounding healthy tissue or adjacent healthy organs.

Conformal radiation therapy has been traditionally approached through a range of techniques, and typically uses a linear accelerator ("LINAC") as the source of the radiation beam used to treat the tumor. The linear accelerator typically has a radiation beam source, which is rotated about the patient and directs the radiation beam toward the tumor to be treated. The beam intensity of the radiation beam is a pre-determined, constant beam intensity. Multi-leaf collimators, which have multiple leaf or finger projections that can be moved individually into and out of the path of the radiation beam, can be programmed to follow the spatial contour of the tumor as seen by the radiation beam as it passes through the tumor, or the "beam's eye view" of the tumor during the rotation of the radiation beam source, which is mounted on a rotatable gantry of the LINAC. The multiple leaves of the multi-leaf collimator form an outline of the tumor shape as presented by the tumor volume in the direction of the path of travel of the radiation beam, and thus block the transmission of radiation to tissue disposed outside the tumor's spatial outline as presented to the radiation beam, dependent upon the beam's particular radial orientation with respect to the tumor volume.

Another approach to conformal radiation therapy involves the use of independently controlled collimator jaws, which can scan a slit field across a stationary patient at the same time that a separate set of collimator jaws follows the target volume as the gantry of the linear accelerator rotates. An additional approach has been the use of attachments for LINACs, which allow a slit to be scanned across the patient, the intensity of the radiation beam in the entire slit being modified as the slit is being scanned.

A further approach for conformal radiation therapy treatment has been the use of a narrow pencil beam of high energy photons, whose energy can be varied. The beam is scanned over the tumor target volume so as to deliver the best possible radiation dose distribution in each orientation of the gantry upon which the photon beam source is mounted.

A major problem associated with such prior art methods of conformal radiation therapy are that if the tumor volume has concave borders, or surfaces, varying the spatial configuration, or contour, of the radiation beam, is only successful part of the time. In particular, when the convolutions, or outer surfaces, of a tumor are re-entrant, or concave, in a plane parallel to the path of the radiation treatment beam, the thickness of the tumor varies along the path of the radiation beam, and healthy tissue or organs may be disposed within the concavities formed by the outer tumor concave surfaces.

In order to be able to treat tumors having concave borders, it is necessary to vary the intensity of the radiation beam across the surface of the tumor, as well as vary the outer configuration of the beam to conform to the shape of the tumor presented to the radiation beam. The beam intensity of each radiation beam segment should be able to be modulated to have a beam intensity related to the thickness of the portion of the tumor through which the radiation beam passes. For example, where the radiation beam is to pass through a thick section of a tumor, the beam intensity should be higher than when the radiation beam passes through a thin section of the tumor.

Dedicated scanning beam therapy machines have been developed wherein beam intensity modulation can be accomplished through the use of a scanning pencil beam of high-energy photons. The beam intensity of this device is modulated by increasing the power of its electron gun generating the beam. The power increase is directed under computer control, as the gun is steered around the tumor by moving the gantry upon which it is mounted and the table upon which the patient lies. The effect is one of progressively "painting" the target with the thickness, or intensity, of the paint (radiation beam intensity) being varied by the amount of paint on the brush (amount of power applied to the electron gun) as the electron gun moves over the tumor. Such dedicated scanning beam therapy machines, which utilize direct beam energy modulation, are expensive and quite time consuming in their use and operation, and are believed to have associated with them a significant patient liability due to concerns over the computer control of the treatment beam.

Other methods and apparatus for conformal radiation therapy have been developed that spatially modulate the beam intensity of a radiation beam across a volume of tissue in accordance with the thickness of the tumor in the volume of tissue by utilizing a plurality of radiation beam segments. Such methods and apparatus utilize attenuating leaves, or shutters, in a rack positioned within the radiation beam before the beam enters the patient. The tumor is exposed to radiation in slices, each slice being selectively segmented by the shutters.

The foregoing methods and apparatus were designed to minimize the portion of the structures being exposed to radiation. However, because exposure to surrounding structures cannot be completely prevented, treatment plans are desired that are optimized to eradicate the tumor volume while minimizing the amounts of radiation delivered to the surrounding structures. Existing methods and apparatus for optimizing treatment plans use a computer to rate possible plans based on score functions which simulate a physician's assessment of a treatment plan.

Existing methods and apparatus utilize a computational method of establishing optimized treatment plans based on an objective cost function that attributes costs of radiation of various portions of both the tumor and surrounding tissues, or structures. One such computational method is known in the art as simulated annealing. Existing simulated annealing methods utilize cost functions that consider the costs of under-exposure of tumor volumes relative to over-exposure of surrounding structures. However, the cost functions used in existing methods generally do not account for the structure volumes as a whole, relying merely on costs related to discrete points within the structure, and further, generally do not account for the relative importance of varying surrounding structure types. For example, certain structure types are redundant in their function and substantial portions of the structure volume can be completely eradicated while retaining their function. Other structure types lose their function if any of the structure is completely eradicated. Therefore, the more sensitive structure volumes can receive a measured dose of radiation so long as no portion of the structure is subjected to a lethal dose.

Existing cost functions utilized in the optimization of treatment plans traditionally have not accounted for such varying costs associated with the different types of structures. After the treatment plan is optimized, the physician must evaluate each computed treatment plan for compliance with the desired treatment objective. If the computed treatment plan does not successfully meet the treatment objectives, the optimization process is repeated until a treatment plan can be computed that meets the physician's treatment objectives for both the tumor volume and the surrounding structures. Further, existing methods and apparatus traditionally have not allowed the physician to utilize the familiar partial volume data associated with Cumulative Dose Volume Histogram ("CDVH") or dose volume histograms ("DVH") curves in establishing the desired dose distributions.

A method and apparatus for determining an optimized radiation beam arrangement for applying radiation to a tumor target volume while minimizing radiation of a structure volume in a patient is disclosed in U.S. Pat. No. 6,038,283, entitled "Planning Method and Apparatus for Radiation Dosimetry, commonly assigned with the present application, and incorporated herein by reference." The method and apparatus uses an iterative cost function based on a comparison of desired partial volume data, which may be represented by CDVHs or DVHs.

Another method and apparatus for determining an optimized radiation beam arrangement for applying radiation to a tumor target volume while minimizing radiation of a structure volume in a patient is disclosed in U.S. Pat. No. 6,393,096, entitled "Planing Method and Apparatus for Radiation Dosimetry."

Many of the foregoing systems replace the traditional forward planning methodology. With forward planning, the user starts by specifying the direction of the beams and their intensities and the computer determines the dose calculations, shows the user what is obtained, and then, based upon to what extent the goals are met, the user goes back and changes the beam parameters. The foregoing systems utilize inverse planning. In an inverse planning system, a professional/user starts with the goals he or she wants to achieve, specifies a prescription for the patient as to how much dose the user would like the tumor to get, and to what degree to spare the other healthy tissue. The computer then calculates all of the various treatment plan parameters, i.e., the direction and corresponding intensity of the beam as it is applied from the different directions. Basically, in inverse planning, the user starts with the clinical goals and lets the computer determine the beam intensities, whereas, in a forward planning system, the user starts with the beam layouts and basically assesses the effectiveness of the plan relative to the goals, and iterates them that way.

In the foregoing system, the user starts from a computerized tomographic ("CT") scan or a magnetic resonance imaging ("MRI") scan. From the CT scan, for example, the user identifies tissue anatomically, typically slice-by-slice, separating what the user wants treated from that which the user wants to spare. For example, the user may identify one item as a tumor, another as the prostate, another as the bladder, etc. Generally, the user will use a pointing device, or mouse, to draw around the area the physician wants to treat in each of a number of slices, since the CT scans provide a set of serial slices of the patient's body. This process can be time-consuming. It would be advantageous, if the tumor is very well differentiated in the CT scan or whatever other image the user selected to examine the tumor, the user could employ an automated tool to allow the user to just "click" on the tumor or target, and automatically determine and mark the location of the boundaries of the tumor.

DVH curves have been used as a prescription and as a feedback mechanism, whereby, the user specifies goals in terms of such DVH curves. The DVH curves represent a summary of how much dose the individual structures are getting. For example, the user may specify the desire for the target to receive a certain minimum dose level delivered to 80% of the target, and also a certain minimum dose level delivered to 90% of the target, as a representation of how the user believes a tumor or target needs to be treated. The computer then develops a treatment plan. After the computer has actually determined how to treat the patient, DVHs are the mechanism for summarizing that treatment and for review by the user. For example, the user requests a specific curve, and the computer then displays the actual curve at the derived treatment plan. The use of the DVH curve in this manner is a familiar, common way of representing such information for plan evaluation by a physician.

To define the DVH prescription, the user typically starts with either a graphical depiction and drags points on a graph on the screen, or enters numbers in the text field boxes. Either way, the user defines the DVH curve. The result is essentially a wish list—a hope that the user can achieve this kind of a DVH curve. After the user completes the proposed DVH curves, the prior systems enter an optimization process that is independent of further user input. This process may typically take at least 10 minutes. The result of the calculations is the return of all of the different "wishes," which may or may not have all been achievable, into an actual plan for treatment. The DVH curves, representing the volumetric statistics of a plan processed by a computer, however, are not manipulatable. It would be advantageous to provide direct manipulation of volumetric to statistics.

DVH curves are a way of summarizing the dosimetric properties of a plan. After inverse planning optimization, the user typically examines the actual DVH curves of the optimized plan. The user can compare DVH curves actually achieved with DVH prescriptions to decide if the developed treatment plan was satisfactory. What is satisfactory may be a question of (1) whether enough dose is getting to enough of the tumor, (2) whether too much dose is getting to some parts of the tumor, and/or (3) how much dose is getting to the healthy structures not identified as tumor. All tissue (target and structures) that can be represented is summarized individually on DVH curves. For example, if the tumor was located in the prostate, the user would be typically provided a single curve on the graph for the prostate, another curve for the bladder, and so on.

One can draw the same conclusions summarized in the DVH curves by actually looking at the CT slices to see the result in more detail. The CT scan slices typically have an overlay showing the various levels of dose applied to discrete portions of each slice. That is, the user can draw conclusions based upon the level of dose applied to any specific organ of interest. In a planning system distributed by NOMOS Corporation, the assignee of the present application under the trademark CORVUS®, the dose in the individual slices is depicted through the use of isodose curves drawn on the CT scan slice. Isodose curves are visually like a contour map of different usually colored lines representing a specified dose level, e.g., 50 Gy, wherein everything inside of the particular curve would be getting at least 50 Gy.

It would be advantageous to decrease the amount of time involved in deciding upon a given treatment plan. Any particular patient might have two or three different treatment plans determined before the user finds a plan believed to be the best. It would also be advantageous if these systems provided the user a more intuitive direct control over what is happening within the plan optimization process that is easier for the user to appreciate.

Traditionally, DVH curves were only used as a form of plan evaluation tool; however, some of the foregoing systems involve drawing DVH curves ahead of time—the users must initially determine the desired goals. It would be advantageous for a computer system to immediately display the user's request and correspondingly display what the planning system can achieve. It would be advantageous for the planning system, if there are compromises to be made between different goals, to display them to the user in a dynamic, interactive manner, and permit the user to dynamically edit the goals and change the terms in which the user would specify a prescription. It would further be advantageous to provide dynamic constraint balancing, i.e., a real-time system for adjusting dosimetric goals while viewing at least one representation of dose in the patient.

Radiation treatment planning includes balancing various, often mutually exclusive, goals. Once these goals are represented, the treatment planning system must know what their relative priorities are in order to balance them optimally. Many current treatment planning systems require the user to explicitly prioritize goals, which may be a difficult, imprecise, and potentially time-consuming process. For example, in "a perfect world," the user may require an entire prostate target to receive 50 Gy, with correspondingly no dose at all to the rectum located 1 millimeter away. This task is virtually physically impossible. So, the issue becomes balancing those two goals and determining which goal is more important than the other. Treatment plans have previously required the user to specify prioritization ahead of time. In some systems, part of what the user is doing when entering DVH curves, is to set priorities between dosing target at a very high level and sparing an organ at risk ("OAR"). Developing such priorities may be a difficult and time-consuming task for the treatment planner. It would thus be an advantage to minimize the need for user-implemented prioritization.

The Applicant has recognized that there are two characteristics that can eliminate the need for user implemented prioritization: First, during interaction with the computer system, an algorithm can effectively consider the user's last input to be the most important requirement. Second, the user can choose to undo the prior input to whatever extent desired. For example, if the user decides to remove, or minimize, a dose from a structure, then priority-wise, that action is the most important requirement. The user may then realize the consequences of that prioritization and may back off on its importance by partially undoing it. This dual prioritization concept is implicit in the interactive process. A computer system and associated algorithms, however, requires an understanding of the relationship of these different goals. As the user layers new goals on top of old goals, the system needs to know how those goals should be balanced. It would be advantageous to provide automatic constraint weighing, i.e., a level of interactivity that in turn permits the prioritization to be inferred from user actions and a sequence of user inputs in the form of plan adjustments rather than direct entry of such priorities; the ultimate result being the elimination from the user's experience the idea of such priorities.

Prior planning systems generally require the user to make adjustments to a patient treatment plan in one of two ways: change delivery parameters (e.g., beam direction and size); or change volumetric dosage goals. It would, therefore, be advantageous to provide for real-time, direct manipulation of isodose contour lines on an isodose plot on a tomographic scan. It would also be advantageous to provide a planning system that allows direct manipulation of deliverable DVH curves rather than indirect specification of potentially impossible, idealized prescriptions.

To some extent, radiation therapy treatment planning is still an art of balance and compromise. It would be advantageous to provide a partial "undo of changes function" to aid a user, wanting to make a plan variation, in the discovery of what sacrifices that a particular change requires. It would correspondingly be advantageous to provide the user with a real-time control permitting the user to dynamically undo a change, completely or partially, and to explore trade-offs, in order to quickly select an optimum balance.

Since developing a radiation therapy treatment plan is an exploration of these trade-offs and other possibilities, some treatment planning systems have shown benefits in providing a means for saving several iterations of a plan for subsequent comparison, and to permit "backtracking." It would therefore be advantageous to provide the user a real-time control permitting the user to establish any two of these plan "checkpoints" as the endpoints on a single continuum and it would be a further advantage to provide the user a means to interpolate between the checkpoints to extract a new version for further comparison or implementation.

In order to interoperate most effectively with other systems, it would be desirable that a new system capable of flexible adjustments, such as that of the present invention, be able to automatically generate treatment goals in its own formulation that would produce a treatment plan identical to one created by another system. This feature would permit a new system to "carry forward" and adjust treatment plans created by other systems. It would thus be advantageous to provide a system with an optimized prescription match function that implements an algorithm, which develops the appropriate treatment goals and their corresponding weights.

In order to permit real-time interactive plan adjustments on current generation computer hardware, the objective function, which the computer frequently optimizes, must be restated in a way which is compatible with rapid optimization without significant reductions in capability. One methodology is to reformulate the goals such that each contributor to the objective function is monotonic in its first derivative. Optimization with monotonic first derivatives of objective contributors basically refers to influence functions, or the terms in a cost function, and it provides a mathematical class of those functions that permits certain computer systems to work calculations quickly. Each objective contributor is formulated in terms of a function of dose. By specifying that the derivative of that function is monotonic, so that the derivative is always either increasing, decreasing, or not changing, never starting out increasing and then decreasing, one can enable a different class of optimization. It would therefore be advantageous to provide a system that utilizes optimization with monotonic first derivatives of objective contributors.

Computing the objective function may be done by effectively sampling the CT or other image of the patient in a number of places to try to capture all of the important aspects of the treatment plan. Speed and interactivity can be improved through use of sampling, which identifies a smaller number of points within the patient at which to simulate the treatment dose. These points must be distributed sufficiently such that the software is "aware" of all important dose features; however, as performance is inversely proportional to the number of such points, one wants to identify the smallest possible group that meets that criteria. It would, therefore, be advantageous to provide a computer system that has an algorithm for automatic selection of minimal plan evaluation points.

A Fluence map is a spatial map of how the radiation is being delivered through a particular position of the delivery device. Plan delivery mechanisms often require that beam fluences take on specific discrete values, whereas optimizers can work in either discrete or continuous space. It would therefore be advantageous to provide an apparatus for converting an optimized plan into a deliverable discrete one.

Different radiation delivery devices will have different constraints upon what they can actually do. For example, one might be able to adjust beamlets that are just a few millimeters across, and one may have to make adjustments that are larger, a centimeter or more across. Another constraint is the degree of variation within a fluence map. For example, the plan map may require 100% of the beam in the middle of the beam to be passing through, and only 50% of the beam in a particular portion to be passing through. Mode fold discretization is a methodology of designing the fluence maps to make the best use of the equipment. Historically, fluence maps are constrained to have certain levels, such as 10% steps, i.e., the delivery device can have a 50% transparency at one point, but not a 52% transparency. These constraints limit the treatment plans that the user can develop. Mode fold discretization assesses a given treatment plan for a patient, and if limited to a discrete number of levels, it determines which of those levels are the optimum. For example, the optimum levels may not be 10%, 20%, 30%, 40% and 50%, but instead may be 13%, 14%, 15%, 80%, and 90%. Mode fold discretization in its basic form takes a histogram of all the desired transmissions (dose levels) in the fluence map, each point representing a set of radiation levels, splits the graph at the peak levels, slides the right side over the left, and adds the overlap points. The process repeats until the algorithm has achieved a particular number of peaks corresponding to the number constrained to by the delivery equipment. Because the actual levels used can have a dramatic effect on both treatment simplicity and speed and the optimal levels for one treatment plan are typically different than those for another, it would be advantageous to provide a "mode fold" discretization algorithm which rapidly estimates the ideal fluence levels for any given treatment field.

Therefore, the art has sought a system, method and apparatus for conformal radiation therapy for treatment of a tumor which: is simple and economical to use; that has what is believed to be a high safety factor for patient safety; computes an optimal treatment plan using simple constraints and a rapid optimizer tuned to them to meet conflicting, fluid, treatment objectives of a physician, accounting for objectives in both the target tumor volume and multiple structure types; and utilizes a graphic user interface ("GUI") displaying isodose contour maps, associated DVH curves, other statistics, and tools allowing the user to establish the desired dose distributions for each target tumor volume and tissue structure type.

SUMMARY OF THE INVENTION

In view of the foregoing, embodiments of the present invention advantageously provide a system to determine an optimal radiation beam arrangement for applying radiation to a tumor target volume while minimizing radiation of a non-target structure volume in a patient. Advantageously, embodiments of the present invention provide a computer planning apparatus that can display immediately a user's request simultaneously with that which the planning system can achieve, and can permit the user to dynamically edit goals and change terms in which the user would specify a prescription. Advantageously, embodiments of the present invention provide for a real-time, direct manipulation of isodose contour lines on an isodose plot on a tomographic scan and direct manipulation of dosimetric statistics, utilizing an input device, and provide the user the ability to adjust individual constraints, preferably one constraint at a time, which in turn causes adjustment to both the isodose contours and the dosimetric statistics.

Advantageously, embodiments of the present invention provide plan matching of an arbitrary/external precedent radiation treatment plan by constructing an optimization objective function having extremum corresponding to the radiation beam configuration of the precedent plan. Advantageously, embodiments of the present invention include a computer planning apparatus that can provide dynamic constraint balancing, i.e., a real-time system for adjusting dosimetric goals while viewing at least one representation of dose in the patient, and automatic constraint weighing, i.e., a level of interactivity that in turn permits the prioritization to be inferred from user actions and a sequence of user inputs in the form of plan adjustments rather than direct entry of such priorities. Advantageously, embodiments of the present invention provide the user with a real-time control permitting the user to dynamically undo a change, completely or partially, and to explore trade-offs between treatment plans, in order to quickly select an optimum balance between versions of a treatment plan and between treatment plans developed on different systems. Advantageously, embodiments of the present invention provide software including an algorithm for automatic selection of minimal plan evaluation points. Advantageously, embodiments of the present invention provide software for converting an optimized plan into a deliverable discrete one.

Embodiments of the present invention provide a system to determine an optimal radiation beam arrangement for applying radiation to a tumor target volume while minimizing radiation of a non-target structure volume in a patient. For example, in an embodiment of the present invention, a system includes a computer planning apparatus which includes: a treatment plan optimization computer having a memory to store data and plan optimization software, therein; and an input device in communication with the treatment plan optimization computer to provide user access to control functions of the plan optimization software. An image gathering device in communication with the treatment plan optimization computer, preferably through a communications network, provides the computer planning apparatus an at least two-dimensional image slice of the tumor target volume and the non-target structure volume. The plan optimization software, which is stored in the memory of the treatment plan optimization computer, computationally obtains a proposed radiation beam arrangement and computationally optimizes a proposed radiation beam arrangement iteratively based on a plurality of constraints to form the optimized radiation beam arrangement. The plan optimization software can include a graphical user interface to display the image slice, graphical objects, and a graphical representation of radiation dose distribution for each proposed radiation beam arrangement. The software is adapted to receive inputs from the input device to manipulate the representations of radiation dose distribution displayed on the graphical user interface. A conformal radiation therapy delivery device, in communication with the treatment plan optimization computer, through the communications network, can apply the optimized radiation beam arrangement to the patient.

The graphical representation of radiation dose distribution can be in the form of an isodose plot including a plurality of isodose contours. The isodose contours of the isodose plot is directly manipulatable by the user to change a radiation dose for the target tumor volume or the non-target structure volume to produce the optimized radiation beam arrangement. The graphical representation of radiation dose distribution can also be in the form of Cumulative Dose Volume Histograms or Dose Volume Histograms, collectively referred to as "DVHs" or "DVH curves," or other forms of dose-volume statistics for the target tumor volume and non-target structure volumes of interest. The DVH plots or curves are directly manipulatable by the user to change a radiation dose, thereby producing the optimized radiation beam arrangement.

The plan optimization software comprises a set of instructions that, when executed by a computer, such as one associated with the computer planning apparatus, causes the computer to perform various functions and operations to develop the optimized radiation treatment plan. The software graphically displays an image slice of the target tumor volume and the non-target structure volume, and graphically displays radiation dose for the target tumor volume and the non-target structure volume on the image slice. The radiation dose can be in a form of an isodose plot including a plurality of isodose contours, according to a first radiation beam arrangement. The isodose contours of the isodose plot are manipulatable by a user to change a radiation dose to the target tumor volume and the non-target structure volume to produce a second radiation beam arrangement.

For example, the software can interface with an input device preferably in the form of a pointing device such as a mouse, or touchscreen, to allow the user to "grab" and "drag" and isodose contour out of or into an adjacent target or structure volume. Also for example, the software can also allow the user to "drop" or "sculpt" a path indicating a desired position for a selected isodose contour. The software, subject to various constraints, attempts to conform the selected isodose contour with the desired path. Further, the software can allow the user to select an isodose contour to be "erased." Functionally, the software, subject to various constraints, sets a value of radiation dose within the selected isodose contour equal or near to a value of radiation dose outside the isodose contour.

The radiation dose can also be in a form of various dose-volume statistics, preferably in the form of a DVH plot or curve, according to a first radiation beam arrangement. The DVH curves are manipulatable by a user to change a radiation dose to the target tumor volume and the non-target structure volume to produce a second radiation beam arrangement. For example, the software can interface with an input device to allow the user to "grab" and "drag" and DVH curves, thereby changing either a percentage of target tumor volume or non-target structure volume permitted to receive more than the predetermined dose level of radiation, or a dose level of radiation, which can be exceeded by a selected percentage of target tumor volume or non-target structure volume.

The user can input a maximum and/or minimum radiation dose the target tumor volume and non-target structure volumes of interest which can be utilized to constrain isodose contour manipulation and DVH curve manipulation to prevent the user from inadvertently causing an undesirable collateral dose variation. The user can also provide a desired balance between maintaining dosimetric quality and maintaining radiation delivery efficiency for a radiation delivery device, which can be used to constrain isodose contour and DVH curve manipulation by the user in order to maintain radiation delivery efficiency above a desired efficiency threshold.

In various embodiments of the present invention, the plan optimization software can: import an externally generated radiation treatment plan; construct an optimization objective function having an extremum corresponding to the radiation beam configuration of that plan; and apply the function to form a radiation treatment plan having a dose distribution approximately the same as the dose distribution of the externally generated radiation treatment plan.

To do so, the software can first form a plurality of target tumor volume sampled points and a plurality of non-target structure volume sampled points by randomly sampling the radiation dose distribution of the plan, with or without bias. The software can then use the value (first value) of dose at these points to form the optimization objective function by adding a term to the objective function for each of the sampled points, each term providing an extremum to the objective function. The terms associated with the target tumor volume sampled points are selected so that the objective function penalizes radiation dose when a second value of the radiation dose at either target tumor volume sampled point of the second radiation treatment plan either substantially differs or substantially undesirably differs from the respective first value of radiation dose. Alternatively, the software can form the optimization objective function by iteratively adjusting at least one of the objective function's constraints.

In various embodiments of the present invention, the plan optimization software can determine an optimized radiation beam arrangement from a pair of radiation treatment plans often referred to as "checkpoints." The software can establish the two checkpoints as endpoints on a single continuum, and responsive to user manipulation of a user-controlled input device, interpolate between the two checkpoints to form and display an intermediate proposed radiation treatment plan. In the preferred embodiments of the present invention, interpolation is linear and is accomplished between the values of radiation dose of the two checkpoints at each corresponding point in the radiation distribution of each plan. This intermediate plan, as with the other plans formed according to embodiments of the present invention, can be easily converted into a deliverable discrete radiation treatment plan through discretization of the plurality of radiation beam intensities into a corresponding plurality of radiation beam intensity settings compatible with a preselected conformal radiation therapy delivery device.

Embodiments of the present invention also include methods of determining an optimized radiation beam arrangement for applying radiation to a target tumor volume while minimizing radiation to a non-target structure volume in a patient. For example, in an embodiment of the present invention, a method includes graphically displaying an image slice of the target tumor volume and the non-target structure volume. The method also includes: graphically displaying radiation dose for the target tumor volume and the non-target structure volume on the image slice and in the form of an isodose plot including a plurality of isodose contours, according to a first radiation beam arrangement defining a first treatment plan; and manipulating at least one of the displayed isodose contours of the isodose plot with an input or pointing device to form and display a second radiation beam arrangement defining a second radiation treatment plan. A related method includes: graphically displaying radiation dose for the target tumor volume and the non-target structure volume in the form of a plurality of dose volume histogram plots according to a first radiation beam arrangement, defining a first treatment plan; and manipulating at least one of the displayed dose volume histogram plots with a pointing device to form and display a second radiation beam arrangement, defining a second treatment plan.

Embodiments of the present invention provide a method to facilitate interactive adjustments to a proposed radiation treatment plan through recalculation and display of two-dimensional radiation dose distributions. For example, a method can include: graphically displaying an image slice of a target tumor volume and a non-target structure volume, and concurrently graphically displaying a radiation dose distribution for the target tumor volume and the non-target structure volume on the image slice and in the form of an isodose plot including a plurality of isodose contours according to a first radiation beam arrangement defining a first treatment plan. The radiation dose distribution in either or both of a target tumor volume and a non-target structure volume can be changed to form a second radiation beam arrangement defining a second treatment plan. Advantageously, to ensure performance, only the two-dimensional dose distribution displayed on the displayed image slice need be recalculated and displayed to provide the user sufficient information to analyze the second treatment plan.

A related method, utilizing sampled points such as those described above, includes: graphically displaying radiation dose for the target tumor volume and non-target structure in the form of a plurality of dose volume histogram plots, defining dose-volume statistics according to the value of radiation dose for the plurality of sampled points; and changing the radiation dose distribution in either or both of the target tumor volume and the non-target structure to form a second radiation beam arrangement. The value of radiation dose at each of the sampled points is recalculated, and the dose-volume statistics for the target tumor volume and non-target structure is displayed according to the recalculated value of radiation dose for the sampled points.

In another embodiment of the present invention, rapid recalculation and display of iterations of a proposed radiation treatment plan is provided by selecting a set of sampled points (randomly or randomly with bias), and applying an optimization objective function constrained by the value of the radiation dose at each of the of sampled points, to form a second radiation beam arrangement. A related method includes selecting a first set of sampled points for plan optimization, and a second set, separate from the first set, for plan evaluation. An optimization objective function constrained by the value of the radiation dose at plan optimization sampled points provides for rapid determination of the second radiation treatment plan, wherein the plan evaluation sampled points provide for rapid display of that second radiation treatment plan.

Embodiments of the present invention also include a method of forming an optimized radiation treatment plan having a fixed set of discrete radiation beam intensity values from a radiation treatment plan characterized by having arbitrary radiation beam intensity values for applying radiation to a target tumor volume while minimizing radiation to an non-target structure volume in a patient. For example, in an embodiment of the present invention, a method includes providing a candidate radiation treatment plan and an optimization objective function to iteratively evaluate the candidate radiation treatment plan. Correspondingly, the method includes iteratively evaluating the candidate radiation treatment plan to form an optimized radiation beam arrangement which both satisfies any preselected clinical goals and has arbitrary radiation beam intensity values, the optimized beam arrangement defining a precedent radiation treatment plan. Utilizing at least two radiation treatment plan iterations evaluated during optimization of the candidate radiation treatment plan, a combination of discrete radiation beam intensities required to substantially match the clinical radiation delivery goals of the precedent radiation treatment plan can be inferred.

In an embodiment of the present invention, rapid calculation and display of a radiation dose distribution for a proposed radiation treatment plan is provided by: forming a plurality of sampled points for a radiation beam arrangement by randomly sampling the first radiation dose distribution; determining a value of radiation dose at each of the plurality of sampled points; and identifying, for each of the target tumor volume and the at least one non-target structure volume, a first set of the plurality of sampled points having the highest values and a second set of the plurality of sampled points having the lowest values. A gradient assent algorithm can then be applied to each first set to determine and to display the radiation dose maximum for the target tumor volume and the at least one non-target structure volume, and a gradient descent algorithm can be applied to each second set to determine and to display the radiation dose minimum for the target tumor volume and the at least one non-target structure volume.

Advantageously, embodiments of the present invention provide a system, method and apparatus for treatment of a tumor which: is simple and economical to use; has what is believed to be a high safety factor for patient safety; computes an optimal treatment plan using simple constraints and a rapid optimizer tuned to them to meet conflicting, fluid, treatment objectives of a physician, accounting for objectives in both the target tumor volume and multiple structure types; and utilizes a graphic user interface ("GUI") displaying isodose contour maps, associated DVH curves, other statistics, and tools allowing the user to establish the desired dose distributions for each target tumor volume and non-target structure volume type.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof, which are illustrated in the appended drawings, and which form a part of this specification. It is to be noted, however, that the drawings illustrate only various embodiments of the invention and are therefore not to be considered limiting of the invention's scope, as it may include other effective embodiments as well.

FIG. 9 is a plan view of a window within a graphical user interface providing a user input of a maximum and/or minimum dose value according to an embodiment of the present invention; and FIG. 10 is a plan view of a window within a graphical user interface displaying results of calculations of a gradient descent algorithm and gradient assets algorithm according to an embodiment of the present invention.

DETAILED DESCRIPTION OF THE INVENTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout, and the prime notation, if used, indicates similar elements in alternative embodiments.

Modern radiation treatment apparatus such as, for example, linear accelerators ("LINACs") radiate a tumor site by making multiple passes along varying arcs approaching the target volume along different entrance paths, each arc being directed toward a point central to a target volume, commonly referred to as an isocenter of the treatment volume. Each pass of the treatment beam will radiate the portions of the tumor and surrounding structures passing within that arc. By utilizing such multiple beam passes, certain portions of the treatment field are irradiated by only some of the beam arcs, while other portions of the treatment field are radiated by each beam arc, thereby causing the highest dose concentration to occur at the isocenter.

Figure 1:
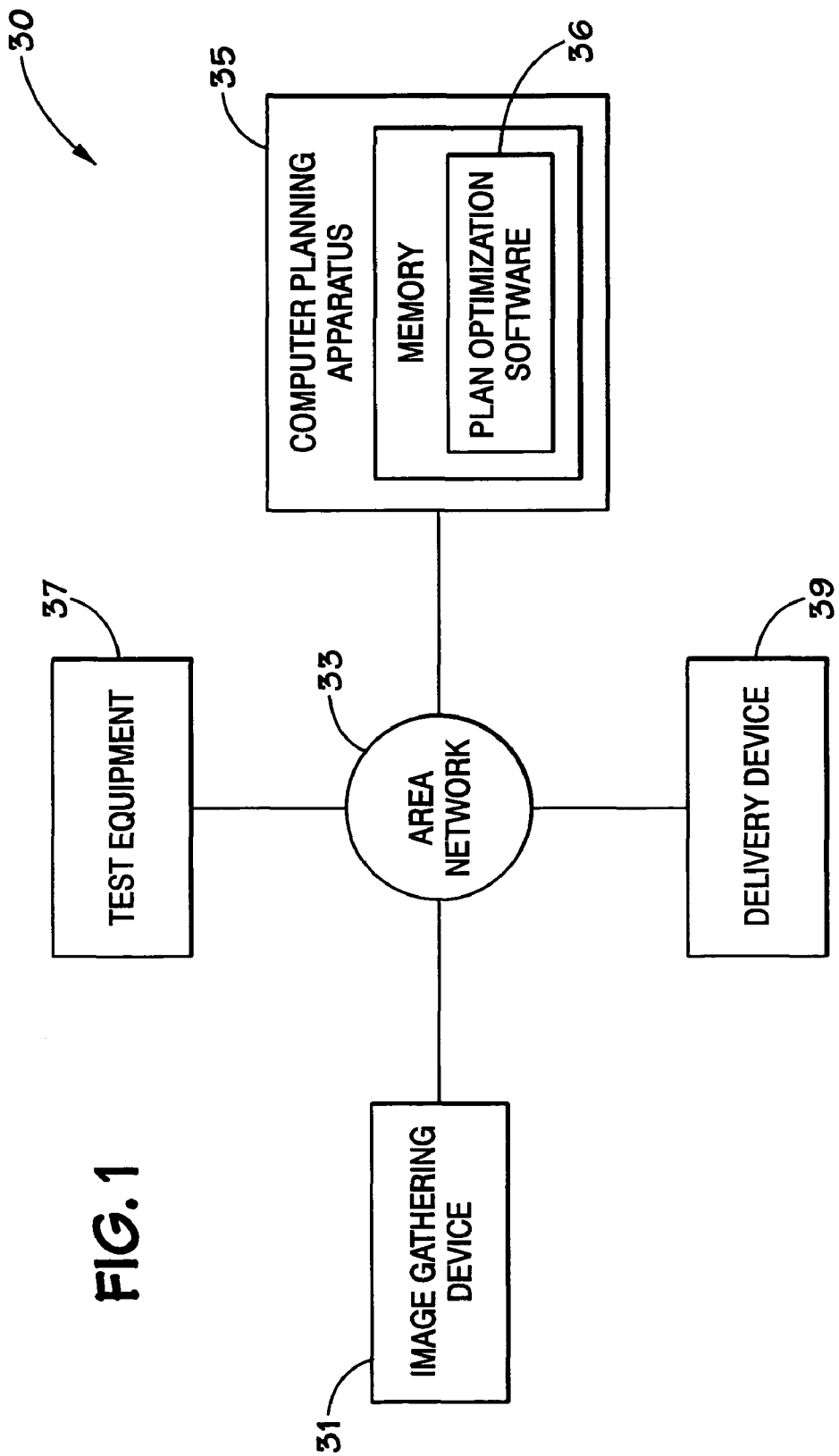
FIG. 1 is a partial schematic view of a radiation acquisition, planning, and delivery system according to an embodiment of the present invention.
Figure 2A:
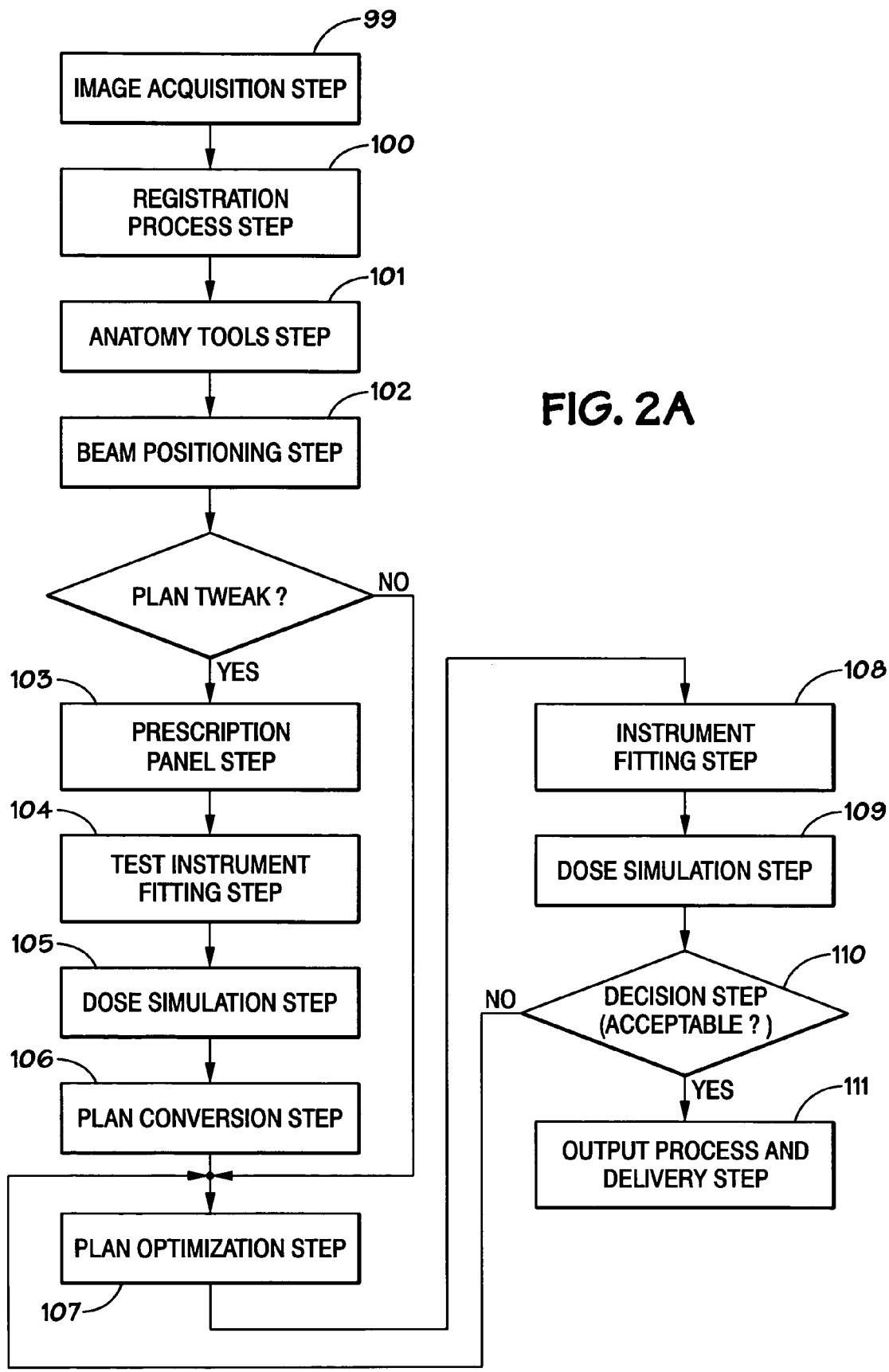
FIG. 2A-C are flow diagrams of a radiation planning system according to an embodiment of the present invention.
Figure 2B:
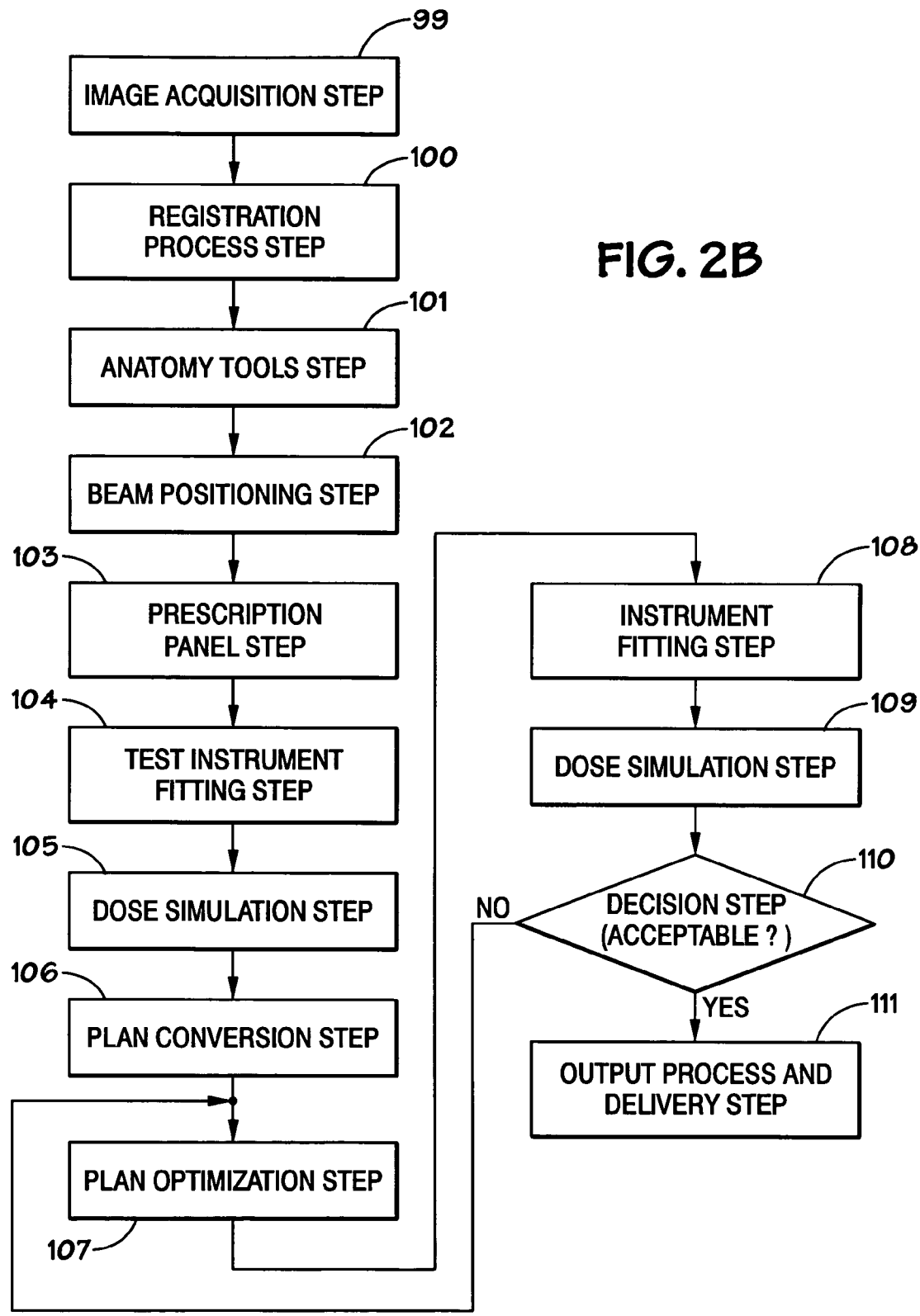
Figure 2C:
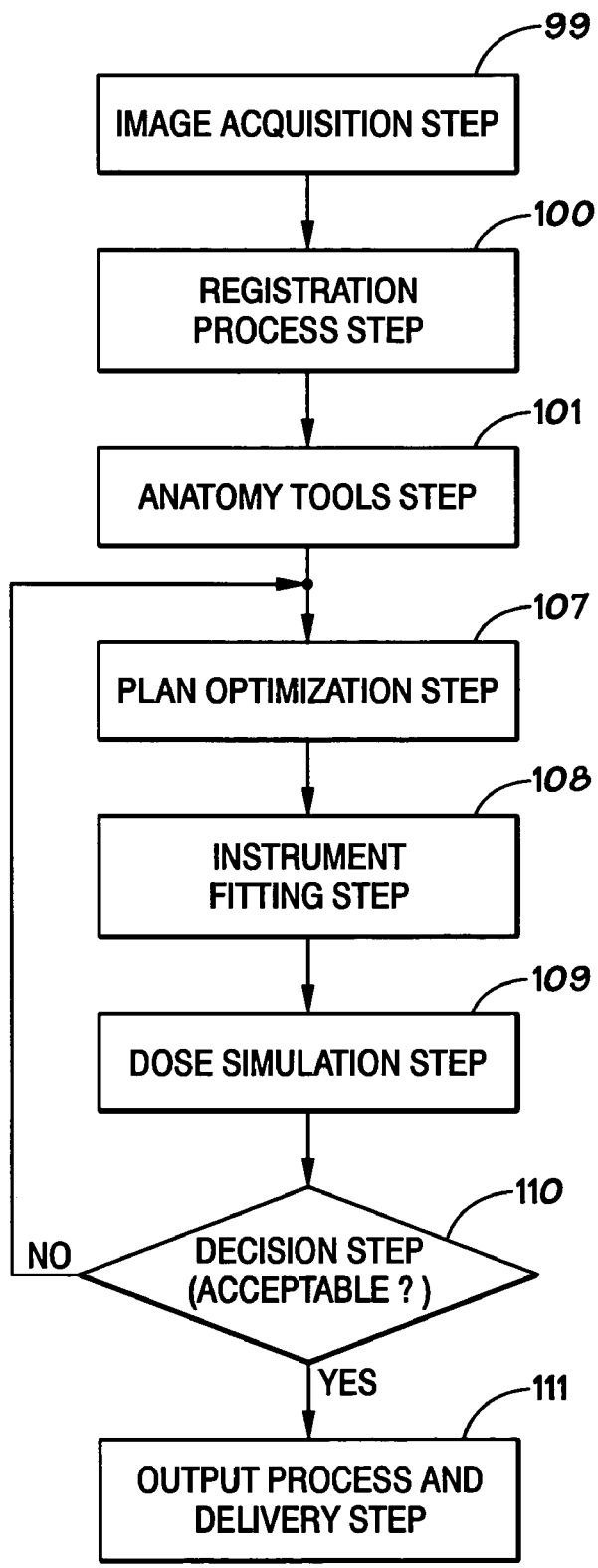
Figure 3:
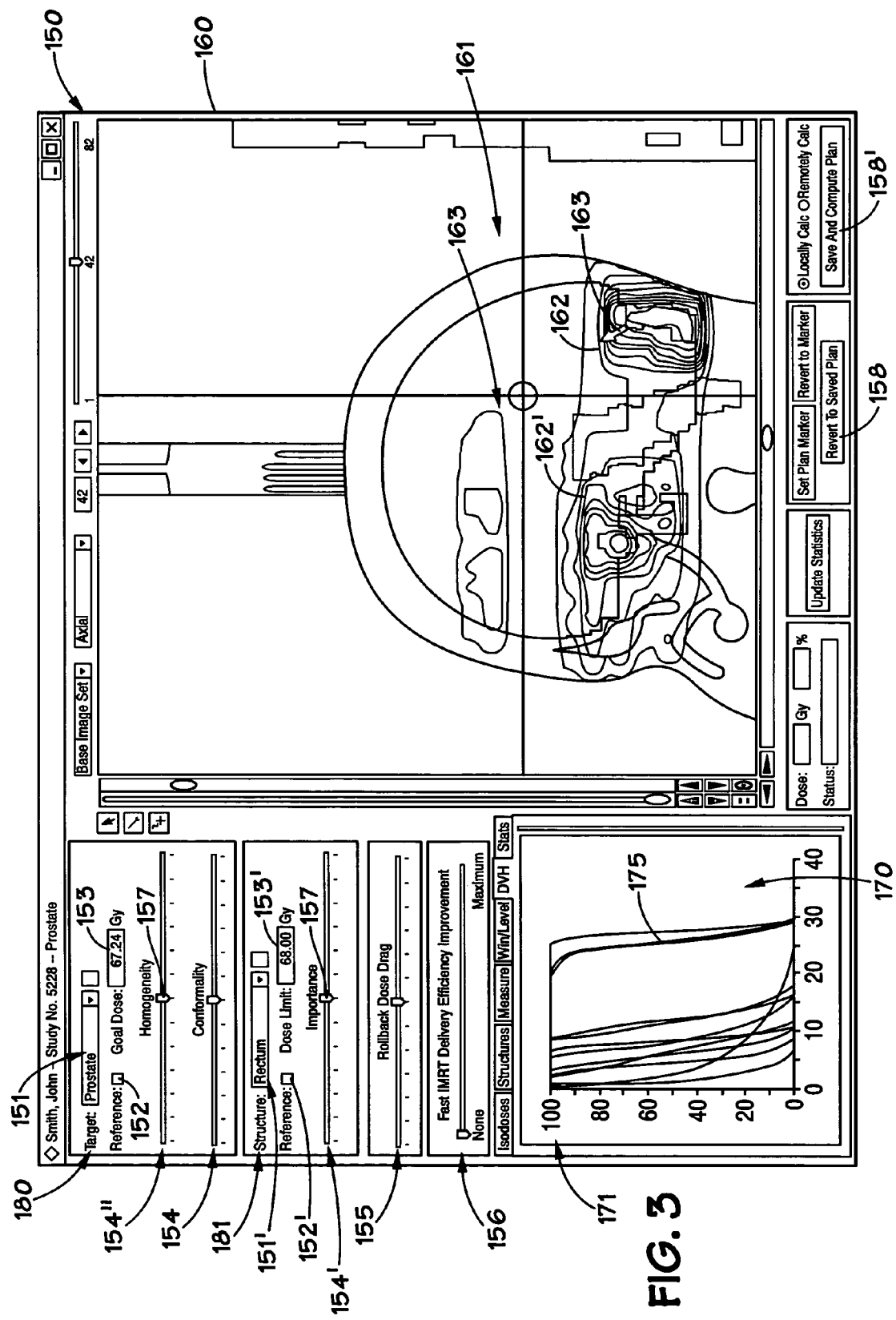
FIG. 3 is a plan view of a graphical user interface according to an embodiment of the present invention.

Embodiments of the present invention, as perhaps best illustrated in FIGS. 1-3, advantageously provide: a radiation treatment planning system 30 for determining an optimal radiation beam arrangement or plan for applying radiation to a tumor target volume while minimizing radiation of a structure volume in a patient; an apparatus for determining and displaying various iterations of the optimal plan; and methods of implementing the system. With reference to FIG. 1, an optimization method of the present invention may be carried out using: an image gathering device 31; a radiation delivery device 39; a computer planning apparatus 35, including a conventional computer or a set of computers; and plan optimization software 36, which utilizes the optimization method of the present invention; and test equipment 37. All of the foregoing components may be interfaced via a conventional area network 33.

The plan optimization software 36 of the present invention computes an optimized treatment plan or beam arrangement, which should be understood to include optimal beam positions around the treatment field, and/or an optimal array of beam weights or beam intensities, otherwise known as an intensity map or a fluence profile or both. The optimal beam arrangement is arrived at initially by computationally increasing the proposed beam weight iteratively and incorporating cost functions to ensure that an iterative change in the beam weight would not result in an unacceptable exposure to the volumes of tissue, or structures, being subjected to the proposed dose. The user may then cause the implementation of additional iterations for added performance.

More specifically, embodiments of the present invention advantageously include an improved optimized radiation treatment planning system 30, which accounts for multiple treatment parameters for both a target and multiple surrounding structure types. The system 30 includes plan optimization software 36 positioned resident on at least one computer: to computationally obtain a proposed radiation beam arrangement; and to computationally change the proposed radiation beam arrangement iteratively based upon at least one constraint type, the constraint type implementing a cost function and a partial derivative function. The system 30 also includes an image gathering device 31 (FIG. 1), such as, for example, a computerized tomographic ("CT") device or magnetic resonance imaging ("MRI") device, to interface with the plan optimization software 36 to provide an at least two-dimensional scan or image 161 (FIG. 3) of the tumor target volume. The system 30 also includes a graphical user interface 150 (FIG. 3) to display the image 161 and provide for user interface options. The system 30 further includes a radiation delivery device 39 (FIG. 1), such as, for example, a LINAC having a multi-leaf collimator or other device known to those skilled in the art for manipulating the radiation beam, to deliver the radiation dose according to the optimization methodologies of the present invention. Note that the software 36 can be in the form of microcode, programs, routines, and symbolic languages that provide a specific set for sets of ordered operations that control the functioning of the hardware and direct its operation, as known and understood by those skilled in the art.

FIGS. 2A-C illustrate methods for creating a radiation treatment plan incorporating the system 30 of the present invention, with FIG. 2A illustrating a general overall flow chart. The system 30 can be implemented in two modes: the first is the FIG. 2B "Plan Tweak" mode wherein the system 30 receives an externally generated precedent plan, adjusts optimization parameters in order to simulate the plan, and then allows for iterative manipulation. The second mode is illustrated in FIG. 2C, and is the "Stand-Alone" mode, which contains a subset of the steps (steps 99-101 and 107-111 of the Plan Tweak mode of FIG. 2B). The first mode, or Plan Tweak mode, will be described in connection with FIGS. 2A and 2B in order to provide a context for the implementation of various embodiments of the present invention. Note that this context is provided for illustrative purposes and should not be interpreted to limit the scope of the present invention.

A first step of forming a precedent radiation treatment plan is typically referred to as the Image Acquisition Step 99. In this step, images are first obtained preferably by conventional CT scanning or MRI techniques, which produce an image 161 representing a "slice" of tissue displayed with anatomical accuracy. The user then either transfers the image 161 directly to the computer planning system 35 (FIG. 1) or to a database accessible by computer planning system 35. This is typically accomplished via the area network 33 (FIG. 1); however, other methodologies, including manual data transfer, can be utilized.

The next step is generally referred to as the Registration Process Step 100. This is the process step of aligning a set of conventional axial slice images 161 of the portion of the patient to be treated by conformal radiation therapy according to the present invention. The series of "slices," which constitute the complete CT or MRI study, represents a three-dimensional picture of a particular portion of the patient, to allow visualization as a valid three-dimensional data set. The resulting data is achieved by sampling the input data, determining common marks of known geometry, and warping the data to be correctly aligned. The resulting resolution is set so that it is geometrically correct based on the known patient fixation device utilized. If the images 161 have been scanned from film, gray scale image normalization is accomplished based on reference graybars included in the images. Conventional two-dimensional image warping techniques, as known and understood by those skilled in the art, are utilized with sampling and filtering as required for resolution adjustment. Image slice spacing is entered by the operator of the computer planning apparatus 35 and verified by the known patient fixation device geometry.

The next step is generally referred to as the Anatomy Tools Step 101. The user identifies the three-dimensional volume of the structure significant to radiation planning, whereby the user identifies the anatomical structures generally on an image slice-by-slice basis. Generally, the user will use an input device (not shown), such as, for example, a light pen, trackball, touchscreen, touchpad, keyboard, or mouse, to draw around the area the physician wants to treat in each of a number of scan slices. In an embodiment of the present invention, the plan optimization software 36 of the computer planning apparatus 35 (FIG. 1) can instead provide an automated tool and associated algorithm to select the tumor boundaries, i.e., if the tumor is well differentiated on the images 161 of the e.g. tomographic scan. The automated tool can allow the user to just "click" on the tool and the software 36 will automatically determine the location of the tumor boundaries.

The next step of the method is generally referred to as the Beam Positioning Step 102. The computer planning apparatus 35 determines an initial treatment plan with corresponding beam positions. The Beam Positioning Step 102 normally precedes the Prescription Panel Step 103.

The Prescription Panel Step 103 allows the physician to input into the planning apparatus 35 the desired goals of the radiation therapy treatment utilized in the prior steps, which, in turn, are utilized in the subsequent Plan Optimization Step 107.

With reference again to FIGS. 2A and 2B, the next step in the method of the present invention is a Test Instrument Fitting Step 104. The resulting optimized set of radiation beam positions and beam weights, or beam intensities for the radiation beam segments, is fitted into the delivery capabilities of delivery device 39 (FIG. 1). An iterative process can be utilized to account for Output Factor (OF) adjustments, the timing of the movement of leaves of the multi-leaf collimator of delivery device 39, and limitations of simultaneous movements to arrive at control information for the delivery device 39 that represent a treatment plan that can be delivered within the operating limitations of the delivery device 39.

In the Dose Simulation Step 105, if implemented, the radiation dose to the patient is simulated based upon, for example, the control information for delivery device 39 (FIG. 1). An algorithm that may be used in this step is based upon the Three-Dimensional Modified Path Length technique, as is known and understood by those skilled in the art.

With reference again to FIGS. 2A and 2B, the next step in the planning method is a Plan Conversion Step 106. The system 30 of the present invention may include several significant departures from current treatment planning practice. For example, the user may interpolate between a plurality of very different treatment plans for the same patient. One of the treatment plans may be created by a CORVUS® system previously identified, another plan may be created by a different system having a different development methodology. In order to interoperate most effectively with other systems, the computer planning apparatus 35 generally must be able to automatically generate treatment goals in its own formulation that will produce a treatment plan substantially identical to one created by another system. This permits the computer planning apparatus 35 to "carry forward" and adjust the various treatment plans created by other systems. An algorithm is provided which develops the appropriate treatment goals and their corresponding weights.

In the "plan tweak" embodiment of the present invention, the computer planning apparatus 35 provides an objective function contributor or "point constraint" unique to this implementation, representing a number of selected sampled plan evaluation points, along with additional constraints, described later. These points are distributed automatically throughout the target and surrounding structures. For example, when the plan matching portion of the computer planning apparatus 35 imports a plan, it can spread the plan evaluation points into selected locations of target boundaries, target interior, organ at risk ("OAR") boundaries, and Dmax points, described later. The distribution is generally accomplished through random sampling. The random sampling, however, can be biased to increase sampled probability in regions of particular relevance, such as, for example, those adjacent the outer boundary of the target tumor volume.

Target tumor volume sampled points and structure volume sampled points can be obtained by randomly sampling a radiation dose distribution or beam arrangement of the treatment plan created by another system. The plan optimization software 36 determines a value of radiation dose at each of the target tumor volume sampled points and the structure volume sampled points. An optimization objective function can then be constructed or modified by adding a term to the objective function for each of the of target tumor volume sampled points and each of the structure volume sampled points. Each term provides an extremum (a minimum or maximum constraint) to the objective function, which corresponds to the radiation beam arrangement of the precedent radiation treatment plan.

Each term associated with the target tumor volume sampled points, or structure volume sampled points, penalizes the radiation dose when a value of radiation dose at either of the corresponding respective sampled points for the proposed radiation treatment plan substantially differs from the respective value of radiation dose for the radiation beam arrangement of the precedent radiation treatment plan. In another embodiment of the present invention, each term associated with target tumor volume sampled points or the structure volume sampled points penalizes the radiation dose when a value of radiation dose at either of the corresponding respective sampled points for the proposed radiation treatment plan substantially undesirably differs from the respective value of radiation dose for the radiation beam arrangement of the precedent radiation treatment plan. Similarly, in an embodiment of the present invention, each term associated with a target tumor volume dose-volume statistic or structure volume sampled points is applied such that the objective function penalizes the corresponding dose-volume statistic when a value of the radiation dose at either corresponding respective sampled points for the proposed radiation treatment plan substantially undesirably differs from a respective value of radiation dose.

After distributing these plan evaluation points, the computer planning apparatus 35 can experiment with different types of cost contributors that could be applied at the different positions, generating the same treatment plan as was imported. In general, absent additional constraints, the computer planning apparatus 35 would not completely succeed in conforming a treatment plan, according to an embodiment of the present invention, into the imported treatment plan, as the imported treatment plan is likely analyzing different points and using different cost contributors. Therefore, the point constraint, described later, provides the computer planning apparatus 35 one other tool to automatically (without being user driven) change and fine-tune a treatment plan to make it substantially similar to the imported plan.

The end result of Plan Conversion Step 106 is that the computer planning apparatus 35 morphs, or converts, a prior plan into a plan properly formatted for use by an optimization engine according to embodiments of the present invention. This can be accomplished by: first determining the radiation beam arrangement (radiation dose distribution) representing original clinical goals used to form the imported radiation treatment plan; and forming an optimization objective function to be used to develop a radiation treatment plan having clinical attributes substantially matching the clinical radiation delivery goals of the precedent radiation treatment plan.

Referring to FIGS. 2A, 2B, and 2C, in the Plan Optimization Step 107, radiation plan optimization is a specific case of an inverse problem, where the goal is to determine an optimum delivery scenario (sets of radiation beams and/or intensities) to achieve the dose prescription. This step is applicable to both the "tweak" (FIG. 2B) and "stand-alone" modes (FIG. 2C). In the "tweak" mode, described above with reference to FIG. 2B, a user runs another planning system, such as, for example the CORVUS® planning system, to generate an optimal plan for that planning system. The plan is then converted or imported for real-time editing utilizing an optimization objective function that can be formed by iteratively adjusting at least one constraint so that the extremum of the optimization objective function corresponds to a radiation dose distribution approximately the same as the first radiation dose distribution, and thus, the original clinical goals, of the imported treatment plan. The user can then run the computer planning apparatus 35 according to embodiments of the present invention in order to "tweak" the imported plan.

Planning system tools, such as those described below, can then be applied to tweak that plan. These new tools can give the user the ability to make more specific requests of the computer planning apparatus, thus providing fine grained, more fluid control over the dose distribution. The imported plan may have been at an optima in the external planning systems cost function. However, because the clinician might have slightly different goals than those embodied in the external system's cost function, the clinician may desire modification to the optimized plan. The new tools provide the clinician the advantage of being able to fine tune a plan, regardless of how it was originally derived.

With reference to the "stand-alone" embodiment of FIG. 2C, the computer planning apparatus 35 enters essentially directly into the stage of interactive planning when the user inputs initial or updated goal information. The computer planning apparatus 35 can relatively quickly (in an interactive time frame), display isodose contours 162 (FIG. 3) and Cumulative Dose Volume Histograms or Dose Volume Histograms, collectively referred to as "DVHs" or "DVH curves" 175 (FIG. 3) from an actual treatment plan that is being developed or modified, both of which can be directly and graphically manipulated by a user.

Instead of sitting down, perhaps spending five or ten minutes writing a prescription, waiting perhaps ten minutes for a plan optimization to be generated, and then evaluating the results and repeating that process, advantageously, according to embodiments of the present invention, the user is provided a more fluid platform that can display a graphical representation of radiation dose distribution for each proposed radiation beam arrangement. For example, the user decides the prostate is to be dosed with 50 Gy, and enters it as such. The 50 Gy dose will then be displayed on the screen around the prostate. The user may then examine the result and decide that an OAR is receiving too much dose. The user may make an adjustment on that particular OAR which resultingly pushes the excessive dose out of the OAR of interest. The user may then again examine the results and make appropriate adjustments. Advantageously, the user is provided the ability to watch the evolution of these iterations as they evolve the radiation treatment plan, thus allowing very detailed, fine tuned adjustments to the plan.

More particularly, as perhaps best shown in FIG. 3, to aid in optimization of the radiation treatment plan, embodiments of the present invention advantageously provide the user an isodose plot 162 on a CT scan, or other tomographic type scan image 161, displayed in scan window 160 of GUI 150. Embodiments of the present invention also advantageously provide the user DVH curves 175. The user is provided a GUI 150 and software 36 which includes algorithms for data entry and manipulation of information displayed on the GUI 150. The GUI 150 can display interactive tools, such as, for example, drop-down menus 151, 151', checkboxes 152, 152', text field boxes, such as, for example, target "goal dose" 153 or structure "dose limit" 153', slide controls 154, 154' for parameters such as target "homogeneity" or structure "importance," respectively, and a screen pointer 163 which, through use of an input device, can manipulate isodose contours 162 displayed in image 161 and/or DVH curves 175.

In an embodiment the present invention, entry of the desired goals can be accomplished via input into an at least one drop-down menu 151, 151', checkbox 152, 152', text entry field 153, 153' of the graphical user interface (GUI) 150 of the computer planning apparatus 35. Goal establishment may also be initiated through the creation and adjustment of prescribed DVHs such as, for example, those illustrated in analysis window 170 (FIG. 3). The prescribed DVHs may be formulated when the user inputs goals into the apparatus 35. Note, in the preferred embodiment of the present invention, the associated DVH curves 175 displaying an achievable radiation treatment plan, can be adjusted via individual or collective manipulation of the various drop-down menus 151, 151', checkbox inputs 152, 152', text entry fields 153, 153' isodose contours 162, and direct manipulation (through use of a pointing device) of the DVH curves 175, themselves.

For example, for a target and structure the user may enter numbers that represent goals such as: (1) target dosage goal value (e.g. 67.24 Gy) in text box 153; and (2) structure dose limit (e.g. 68 Gy) in text box 153'. For both the target and structure, the GUI 150 can display a small graph or slide bar 157 that functions to allow the user to "drag" the bar 157 along the length of slide control 154, 154', to establish the same result described by entry of the numbers in the text boxes 153, 153'.

The computer planning apparatus 35 can apply simple constraints and a rapid optimizer tuned to them, which together provide a context for direct manipulation of isodose contours or contours 162, and dynamic balancing of conflicting goals. Ideally the objective function contributors, or constraints, are continuous and have first derivatives that are monotonic, and implement cost functions that are piecewise linear. The computer planning apparatus 35 can turn a radiation treatment plan into a "score" S, which equals the summation of the value of the individual cost contributors multiplied by their assigned priority, or weight, wherein:

$$S = \sum_{x=1}^{n} W_x C_x;$$

where $C_x$ is a cost contributor, n represents the nth contributor, and $W_x$ is the priority or weight assigned to the nth cost contributor. These cost contributors, or influence functions, may take the form of constraints, which are in turn a function of the radiation beam weights or dose. In the preferred embodiment, the treatment plan "score" S hereinafter described is a function of the cost contributors which are in turn comprised of at least, but not limited to, one or more of the following constraints:
 1. Target boundaries;
 2. Target interior/target coverage;
 3. Organ at Risk (OAR) boundaries;
 4. $D_{max}$ points: located at the $D_{max}$ point of each beam; and
 5. Drag up/down points: these points lie along a line drawn by the user.
 6. Point constraint (plan matching embodiment only).

Each of the constraint types are broken down by where the respective points of interest for the respective constraints are located and the area of interest within the patient. Each of these constraint types must implement a cost function and a partial derivative function (with respect to a specific beam fluence). Details of the effect of the constraints are hereinafter described. The beam weights effectively describe the radiation treatment plan, and the cost function evaluates the radiation treatment plan by producing a score, wherein any individual cost contributors, or constraints, may be a function of a subset of the radiation beam weights. Also, only the voxels associated with constraints (constraint voxels), are dosed while costing during iterations of optimization.

Still referring to FIG. 3, in the preferred embodiment of the present invention, the computer planning apparatus 35 can provide dynamic constraint balancing, i.e., a real-time method for adjusting dosimetric goals while viewing at least one representation of dose in the patient, as for example, an isodose plot 162 on a CT scan, or other tomographic type scan or image 161, displayed in scan window 160 of GUI 150. In this embodiment, software 36 includes algorithms for the dynamic manipulation of a radiation treatment plan through the use of user interactive tools, such as, for example, the drop-down menus 151, 151', checkboxes 152, 152', text field boxes 153, 153,' slide controls 154, 154', and screen pointer 163 positioned to manipulate the DVH curves 175 an the isodose contours 162 displayed in image 161.

The evaluation of the various iterations of a radiation treatment plan generally requires a sampling of plan evaluation points throughout the patient. This sampling can be either completely random, or random but with a bias, to increase sampled probability adjacent the outer boundary of the target tumor volume, which can advantageously provide more information utilizing less plan evaluation points. To add reliability to the plan evaluation, the plan evaluation points selected are preferably not the same randomly selected points utilized by the plan optimization software 36 of the computer planning system 35 (FIG. 1) to perform and display the various iterations of the radiation treatment plan.

The foregoing described constraints can provide the applicable mathematical structure to efficiently perform the development and evaluation of the radiation treatment plan. Further, software 36 of the computer planning apparatus 35 can provide the above-described constraints, along with others known to those skilled in the art, whereby such constraints are functionally set to penalize the score S of the plan, or make the plan less attractive.

The first two of the constraints identified above are target boundaries and target interior/target coverage. Target boundaries signify the form of the tumor. An algorithm of software 36 implements this constraint by examining plan sample points along the boundary of the target. A plan that sets the boundaries, either inside or outside the actual boundaries, will produce a plan that is more desirable to the user. A visual depiction of this influence function basically takes the form of an upside-down notch which is piecewise linear, and is described by those skilled in the art as creating wells driving their associated voxels towards the prescription dose. Additionally, a slide control 154, or other form of adjustment control, is provided to adjust the weight or importance of correct selection of boundaries to the overall plan.

The target interior constraint is provided to ensure the target is given at least a minimum dose. This constraint penalizes the plan where dose in the target voxels are below the goal dose and thus attempts to drive the dose up. The target coverage constraint, which can be a separate constraint or combined with the target interior constraint, is also provided to ensure the entire target gets a minimum dose and is homogeneous. This constraint, however, penalizes the plan where dose in the target voxels are above the goal dose and thus attempts to drive the dose down. In the preferred embodiment, a slide control 154" similar to slide control 154 or other form of adjustment control, is provided to adjust the importance of these constraints.

The OAR boundaries constraint is provided to ensure a healthy organ is not exposed to an excessive dose of radiation, i.e., beyond that of the dose limit. The constraint penalizes an excessive dose in the OAR voxels. In the preferred embodiment, a slider control 154' or other form of adjustment control is provided to adjust the importance of this constraint.

The $D_{max}$ points constraint describes the point along each beam where the dose is highest as a result of that particular beam. The $D_{max}$ points constraint is provided to control dose that is not in the target. In the preferred embodiment, an algorithm of software 36 is provided that ignores any of the points that fall in a target, and adds any of the points to the "OAR boundary" voxels that fall within an OAR.

The drag up/down points constraint is defined by a set of points along a line drawn by a user. In the preferred embodiment, an algorithm of the software 36 is provided to drive the dose either above or below a threshold—above when the line is started on a point where dose is higher than the average dose along the line, or below when the average is higher. A meta-optimization can balance the strength of these constraints to ensure they are just strong enough to be satisfied.

In the preferred embodiment of the present invention, the computer planning apparatus 35 can provide automatic constraint weighing. Treatment planning consists of balancing various, often mutually exclusive goals. Once these goals are represented, the treatment planning apparatus 35 must know what their relative priorities are in order to balance them optimally. As stated previously, many treatment planning systems require the user to explicitly prioritize goals, which may be a difficult, imprecise, and a potentially time-consuming process. Conceptually, the computer planning apparatus 35 and associated algorithms require an understanding of the relationship of the different goals encapsulated by the treatment plan, and as the user layers new goals on top of old goals, how those goals should be balanced. Advantageously, embodiments of the present invention can provide automatic constraint weighing, i.e., a level of interactivity that permits prioritization to be inferred from user actions and a sequence of user inputs in the form of plan adjustments, rather than through direct entry of user determined priorities. The software 36 of the computer planning apparatus 35 can translate an inferred priority into a numerical value that determines the internal "weight" given to a particular goal. Automatic constraint weighing is a methodology whereby each time a user adds a new goal and makes adjustments, an algorithm assigns a certain level of importance to that new goal, maintains another group of goals, e.g. 50 goals, at their own separate levels of importance, and calculates those importances in a way that is seamless to the user. In the preferred embodiment, a simple search methodology, executing a separate optimization at each search trial, provides this automatic translation.

In an embodiment of the present invention, with reference to FIG. 3, actual implementation of prioritization can be obtained from the use of a slider control, such as, for example, slide control 154 and/or use of a conventional pointing device (not shown), which operates a screen pointer 163 to directly manipulate ("drag") the dose represented by either isodose contours 162 or DVH curves 175. For example, from the user's perspective, a sensitive tissue sparing slide control 154' can be used to take dose out of a structure which can be viewed by the software 36 as the equivalent of setting an absolute goal of zero dose in the structure. Within the confines of the software 36, however, the addition of a new goal is actually tantamount to adding a new term to a total cost function comprised of a series of weighted cost contributors, and/or changing the weights of the others. Further, according to an embodiment of the present invention, dragging a dose (isodose contour 162 or DVH curves 175) adds a new term to the total cost function; and controlling a slider control 154, for example, pushing dose out of an organ, changes one of the pre-existing terms.

Still referring to FIG. 3, in the preferred embodiment of the present invention, goal adjustment can be accomplished via interactive plan dose modification: direct manipulation of the isodose contours 162 (often referred to as an isodose "contour map") and direct manipulation of the DVH curves 175, wherein the output would then be the change to the isodose contours 162 and to the DVH curves 175. In an embodiment of the present invention, the approximate DVH of the targets and the abscissa-intercept of OAR DVHs, and/or estimated maximum dose of OARs, are dynamically updated. In another embodiment of the present invention, they are "snapped" to full-detail by a low-priority thread that tries to update them during idle periods.

Referring to FIGS. 3, 4, 6, 7, and 8, in the preferred embodiment of the present invention, there are at least five major choices provided to the user for pushing dose out of a tumor volume or adjacent structure volume. The first choice provides a global adjustment to the affected tumor volume or tissue structure. For example, the user can tab, or select, a tissue structure affected by the dose, e.g. the whole rectum. The structure can be selected from a drop-down menu 151'. The user can adjust the associated slider control 154' to reduce dose in the effected structure or enter a reduced dose value in an associated text box 153'. The adjustment, however, may or may not change dose in any specific part of the affected structure, but would focus on whatever was the "hottest part" of the affected structure, or portion of the structure receiving the greatest dose. If the hottest part was also the part of concern to the user, the adjustment should be effective. If the area of interest is not the hottest part of the affected structure, the adjustment would affect another part of the affected structure at, or before it affects, the point of interest within the structure. Instead of using slider control 154', the user may instead examine the isodose contour plot 162 on the CT or other tomographic type scan 161 of scan window 160 of GUI 150, described below.

Figure 4:
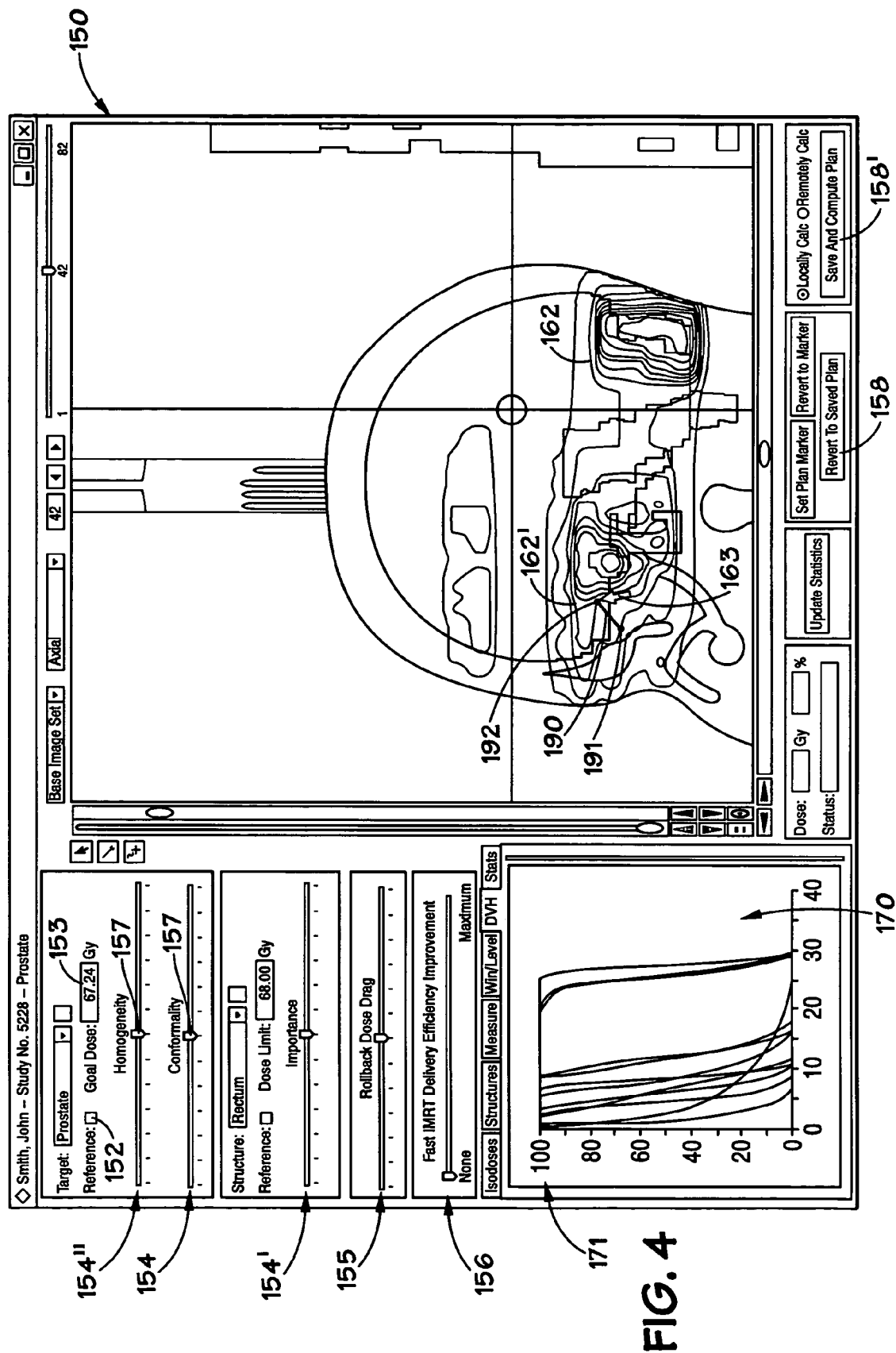
FIG. 4 is a plan view of a scan display window within a graphical user interface according to an embodiment of the present invention.

The remaining user choices are more flexible and tend to be more localized in response. Referring to FIGS. 3 and 4, the user can examine the GUI 150 comprising scan window 160 which includes isodose contours 162 overlaid or drawn across the affected structure; e.g. the rectum. As previously described, the isodose contours 162 correspond to the dose commonly delivered to a portion of the target or structure. The GUI 150 provides direct manipulation of those isodose contours 162 on, for example, the CT slice 161. The user can be provided the ability to manipulate the isodose contours 162 through use of a conventional pointing device (not shown) or other suitable input device known and understood by those skilled in the art, which can be represented by screen pointer 163. The software 36 includes an algorithm that allows the user to "grab" and "drag" an isodose contour 162 to a selected location. Radiation, however, does not just let one make an isolated change. Other parameters will correspondingly change when the user releases the "grab" of the pointing device on the isodose contour 162 of interest. This release commands the algorithm to output a new plan wherein the adjusted isodose contour 162 forms an added constraint. The new isodose contour "contour map" provides the primary feedback resulting from dragging the isodose contour 162 of interest.

Direct manipulation of one isodose contour 162 may cause that isodose contour 162 or another isodose contour 162' at a different location to bulge out. Through this visualization, the user can then determine whether the change, due to the unrequested deviation, is detrimental, and if so, to what extent. Referring to FIG. 4, the isodose contour 162' representing the deviate dose can be selected or "clicked on" and dragged across or out of the affected structure. For example, the user may click on that isodose contour 162' and drag it out of the rectum. Upon release of the point device, or mouse button (not shown), the computer planning apparatus 35 will recalculate another new plan based upon everything the user previously requested with a constraint that that dose does not get into the previously affected structure, as for example, the rectum. In this alternative, only the "hotspot" of interest is primarily affected by the adjustment, rather than the entire target or structure. The conceptual affect of dragging an isodose contour 162 of interest is to vary the way that the isodose contours 162, 162' curve through the patient.

Note that a "normal" optimization process optimizes radiation beam direction and/or intensity within the bounds of user defined constraints. A meta-optimization process, instead, can iteratively adjust the constraints themselves to achieve goals coinciding with those of the imported treatment plan. A meta-optimization can balance the strength of the above-described constraints so as to ensure they are just strong enough to be satisfied. Further, responsive to input of a maximum and/or minimum dose value 164, 165 (FIG. 9), the software 36 can constrain isodose contour manipulation by the user to prevent an undesirable collateral dose variation, such as that described above.

Still with reference to FIG. 4, dragging the dose mathematically forms a line 190 between the start dragging point 191 and the stop dragging point 192. Computationally, an algorithm of software 36 of computer planning apparatus 35 attempts to ensure that that particular isodose contour 162' of interest doesn't cross line 190 formed by the dragging. That is, a constraint established along the line 190 can be implemented to constrain the dose along the user selected line to a value level not to exceed the desired level of dose where the undesirable level of dose is greater than the desired level of dose, and implemented to constrain the dose along the user selected line to a value level not below the desired level of dose where the undesirable level of dose is less than the desired level of dose.

This objective can also be accomplished where the undesirable dose is between the start and stop dragging points 191, 192, by averaging the dose along the line 190 from the start dragging point 191 to the ending point 192. The algorithm then drives the dose up when the line 190 is started on a point with a dose higher than average dose along the line 190, and lower when the average is higher. For example, if a peninsula of dose is protruding into an organ, the start point 191 may be at an isodose contour 162' of, for example, 70 Gy. The line 190 may be formed by dragging that isodose contour 162 across another isodose contour 162" of, for example, 80 Gy, ending at a stop point 192 of 70 Gy. If the average along the line is 73 Gy, the average dose would be higher than at the starting point, so the algorithm would assume the user wishes to push the dose down along that line.

In another example, the user desires to push a "hotspot" out of a portion of healthy tissue structure using the "dragging the dose" alternative. The user drags the dose by engaging an isodose contour 162 with the point device associated with screen pointer 163 and drags the isodose contour 162 across and over the "hotspot." This process resembles grabbing a contour line of a contour map and dragging the contour line over the top peak of the mountain depicted on the contour map, i.e., the user places the point device somewhere just outside of the peak contour, drags across the peak, and releases the repositioned contour line on the opposite side of the peak.

The associated algorithm of software 36 can establish a constraint along the line 190 such that nothing along that line 190 between the two points 191, 192, receives a level of dose higher than noted when the user initially started dragging. Ideally, as stated in this example, the algorithm would remove the peak of the mountain. If, however, the peak was very broad, the user action may only carve a new valley along and on either side of line 190. If so, the user can either make additional attempts, or consider an alternate methodology, such as, for example, the global slider control method, described above. Note, correspondingly, where the user instead desires to extend an isodose contour line to increase radiation dose in a nearby area, the associated algorithm of software 36 can establish a constraint such that nothing along a line formed between the start-drag point and end-drag point receives a dose less than that of the start-drag point.

Figure 6:
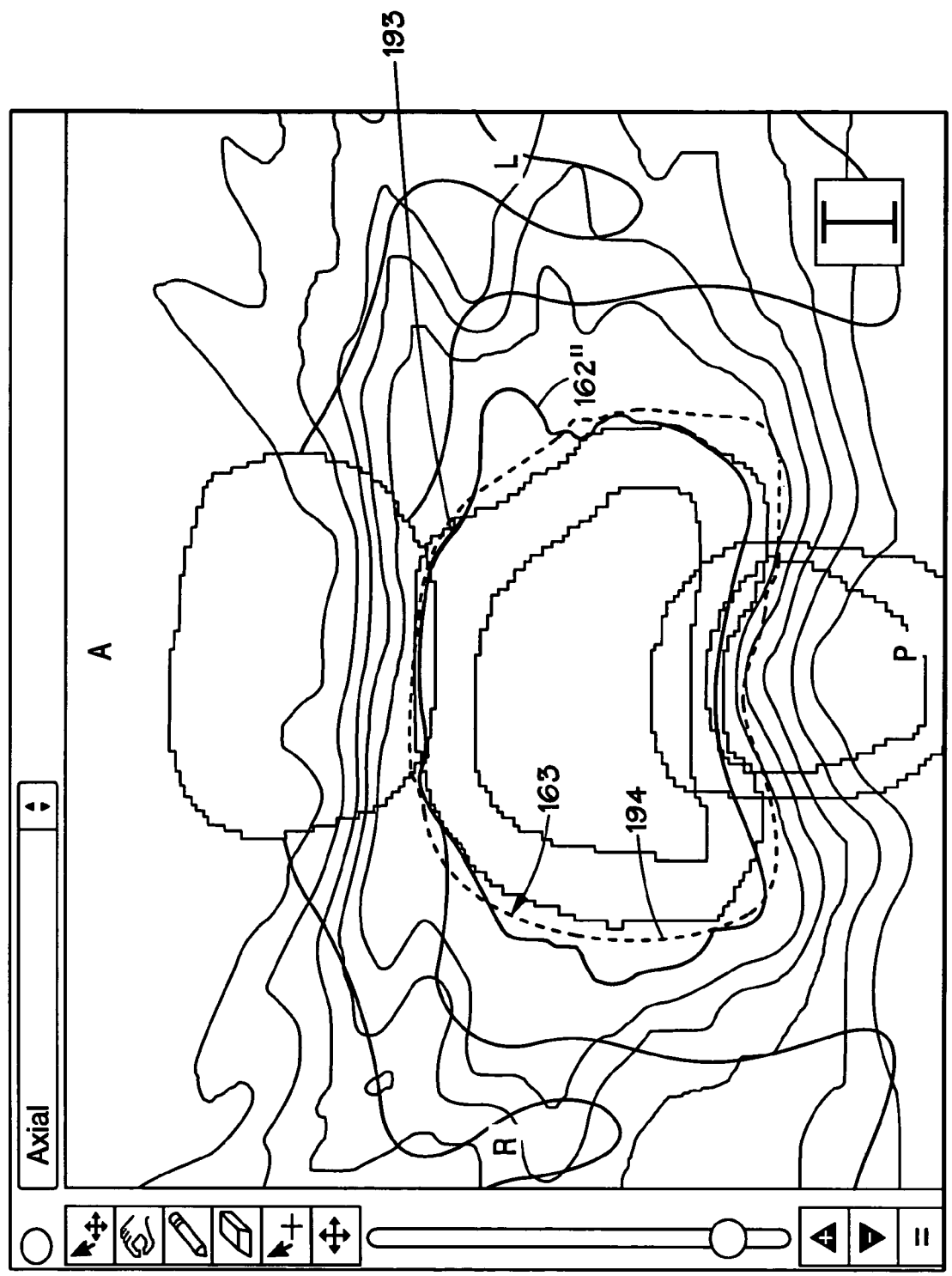
FIG. 6 is a plan view of a graphical user interface according to an embodiment of the present invention.

As perhaps best shown in FIGS. 3 and 6, the software 36 can include an algorithm that (1) allows the user to "select" or "mark" a portion 193 of an isodose contour 162" or other isodose representative value on the image slice 161, having a user desired level of dose; and (2) allows the user to manipulate or "drag" a user input device, to "draw" or "sculpt" a proposed isodose contour along a user desired path 194 (illustrated as a dashed line) from the selected position 193 to a second selected position on the image slice 161, preferably near or adjacent the isodose contour 162". Responsive to the selection and the user manipulating the input device to form the user desired path 194, the software 36 repositions the isodose contour 162 approximately adjacent the user desired path 194, thereby reforming the isodose contour 162", and thus, forming a new radiation beam arrangement. As with isodose contour manipulation, described above, preferably release of the input device commands the algorithm to output the new plan, wherein the adjusted isodose contour forms an added constraint.

Note that the software 36 can include provisions for constraining the above two described methodologies of isodose contour manipulation to prevent an undesirable collateral dose variation. The user can input either or both of a maximum and a minimum radiation dose value 164, 165 (FIG. 9) for a target tumor volume or a structure volume. Responsive to input of the maximum and/or minimum dose values 164, 165, by the user, the software 36 prevents movement of the isodose contour 162" that would result in a radiation dose deviating from outside the user provided dose constraints.

Figure 7:
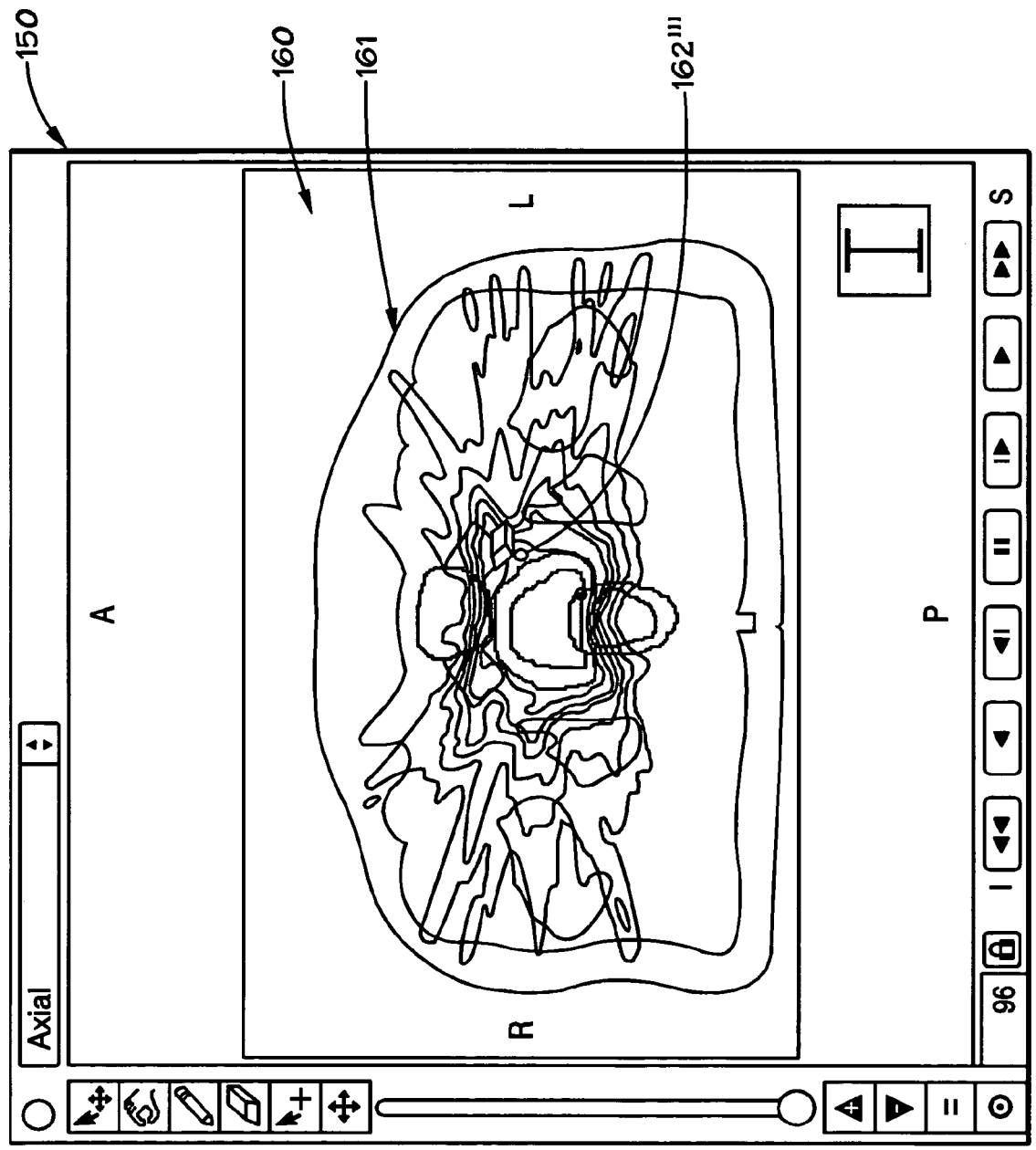
FIG. 7 is a plan view of a graphical user interface according to an embodiment of the present invention.

As perhaps best shown in FIG. 7, the software 36 can include an algorithm that provides a tool which allows the user to "select" or "mark" an isodose contour 162''' to functionally "erase" a high radiation anomaly or hotspot (illustrated), a low radiation anomaly, or to perform a more global maximum dose reduction. For a high radiation anomaly, responsive to the user selecting the isodose contour 162", the software 36 can set a value of radiation dose, within the isodose contour 162''', approximately equal to a value of radiation dose outside the isodose contour 162'''. For a low radiation anomaly, the software 36 can set a value of radiation dose within an isodose contour 162''' approximately equal to the value of radiation dose outside the isodose contour 162'''. In either situation, the shifting of dose within the isodose contour 162''' conceptually erases the isodose contour 162'''.

As with the above described two forms of isodose contour manipulation, release of the input device preferably commands the algorithm to output a new plan, wherein the change in value of the isodose contour 162''' forms an added constraint. Also, as with the above described two forms of isodose contour manipulation, the software 36 can also include provisions for constraining this methodology of isodose contour manipulation to prevent an undesirable collateral dose variation. The user can input either or both of a maximum and a minimum radiation dose value 164, 165 (FIG. 9) for a target tumor volume or a structure volume. Responsive to the input of the maximum and/or minimum dose value 164, 165, by the user, the software 36 can prevent any change in dose within the selected isodose contour 162''' that would result in a radiation dose deviating from outside the user provided dose constraints.

Figure 8:
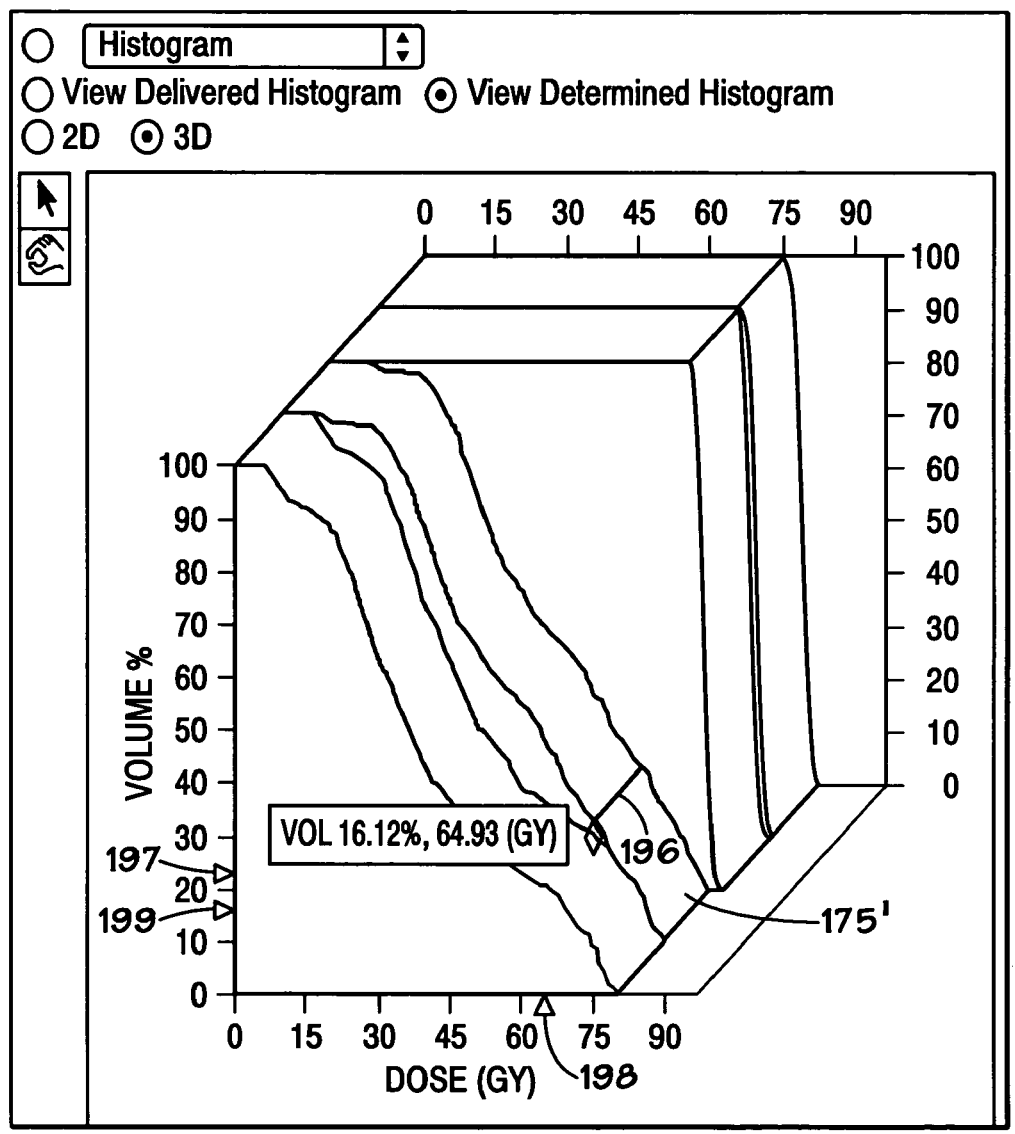
FIG. 8 is a plan view of a graphical user interface according to an embodiment of the present invention.

As perhaps best shown in FIGS. 3 and 8, the software 36 can include an algorithm that allows the user to "grab" and "drag" a DVH curve 175' to either reduce/increase a percentage of tumor volume or structure volume receiving more than a predetermined dose level of radiation, as illustrated in FIG. 8, reduce/increase the level of the excessive dose for a given percentage of tumor volume or structure volume, or an intermediate combination, therebetween. Utilizing an input device preferably in the form of a pointing device, the user can select a portion of a DVH curve 175' located at a selected position 196 which indicates a percentage 197 of target tumor volume (or adjacent structure volume) permitted to receive more than a predetermined dose level of radiation 198. Responsive to the user dragging the selected portion 196 of the DVH curve 175' with the input device along a user desired path to another location, the software 36 alters the percentage 197 of the target tumor volume (or adjacent structure volume) permitted to receive more than a predetermined dose level of radiation, thereby forming the new radiation beam arrangement having a user desired percentage 199 of target tumor volume (or adjacent structure volume) permitted to receive more than a predetermined dose level of radiation.

As with isodose contour manipulation/erasure, described above, preferably release of the input device commands the algorithm to output the new plan, wherein the adjusted DVH curve 175' forms an added constraint. Also, as with isodose contour manipulation/erasure, the software 36 can also include provisions for constraining this type of DVH curve manipulation by the user to prevent an undesirable collateral dose variation. The user can input either or both of a minimum and a maximum radiation dose value for a target tumor volume or a structure volume. Responsive to the input of the maximum and/or minimum dose value 164, 165 (FIG. 9) by the user, the software 36 can prevent any change in dose that would result in a radiation dose deviating from outside the user provided dose constraints.

Referring again to FIG. 3, in an embodiment of the present invention, the user is provided a slide control 155 that allows a partial undo, or unroll, of the change prompted by the dragging of the isodose contour 162. As noted above, when the user drags the isodose contour 162 of interest and then releases it, the user causes the isodose contours "contour map" to redraw in the scan window 160 a new picture of the radiation treatment plan ("checkpoint"). Thus, the user is presented with information necessary to determine the effect of the "proposed" change. Conceptually, the user has requested a change in the radiation treatment plan without the knowledge of what the compromises would be or what the changes would involve. The user, nevertheless, generally needs to appreciate what has collaterally changed and how the proposed modification affected the collateral change. Thus, the user is presented with slide control 155 (partial undo slider), wherein the user may slide the handle 157 of the slider 155 to incrementally "back-out" of the proposed modification. Although other methodologies are within the scope of the present invention, the function of the slider 155 is preferably achieved through linear interpolation between dose values (corresponding to linear interpolation of beam intensities) of the sampled points utilized by the plan optimization software 36, described in more detail later.

The partial undo slider 155 is basically equivalent to a backspace device that automatically encapsulates the last adjustment the user made. Further, in the preferred embodiment, the partial undo slider 155 defaults with its handle 157 in the far right position upon release of the isodose contour 162 of interest and scan window 160 corresponding displays the modified plan. If the user slides the slider handle 157 all the way to the left, the algorithm undoes the modification completely. Sliding the handle 157 back to the right, re-institutes the modification completely so that the user may, in real time, realize the effect of the modification, fully or incrementally, as the user slides the handle 157 back and forth. Advantageously, the user may more readily understand the extent of the compromises. The user may select any intermediate point to view the plan configuration before the adjustment and the result of the adjustment.

For example, the user reviews the isodose contours 162 overlaying image 161 in scan window 160 of GUI 150 and determines that an excessive dose is being delivered to a healthy organ structure, such as the rectum. The user enlists the pointing device associated with screen pointer 163 and grabs the isodose contour 162 of interest, correspondingly pushing the dose all the way out of the rectum. In this example, assume the adjustment resulted in less than desirable results in collateral areas. The user, unhappy with the result of the adjustment, then experiments with the adjustment by moving the handle 157 of partial undo slider 155 back and forth, examining the isodose contours 162 changing on the screen with each increment. As the user moves the handle 157 of partial undo slider 155, causing the isodose contours 162 to "fluidly" move in and out of the rectum, the user selects the isodose contour location corresponding to the best possible compromise. Upon release of the handle 157 of partial undo slider 155, the algorithm provides the updated treatment plan. The user then continues with an examination of the results and correspondingly makes other changes.

In embodiments of the present invention, the computer planning apparatus 35 provides an ability to interpolate fluence maps. This ability provides the user the flexibility of examining the full range of options between a plurality of reference plan scenarios. For example, in an embodiment of the present invention, the partial undo algorithm implements a dynamic slide control 155 that, as discussed above, has the effect of allowing the user to quickly perform a partial undo of changes. In its simplest form, the partial undo of changes function allows for the creation of an average treatment plan, that is, for example, equivalent to a plan scenario that is conceptually "halfway" between the pre-adjustment plan and post-adjustment plan. The associated algorithm can average the dose (interpolation between dose matrices) and average the fluence patterns (interpolation between beam intensity profiles) from which the dose of interest is derived. As long as the algorithm is limited to a certain set of constraints, the algorithm can perform this operation responsively, and will produce a treatment plan selected within the continuum between the preadjustment treatment plan and the post-adjustment treatment plan. In the various embodiments of the present invention, the computer planning apparatus 35 provides differing levels of such limitations on constraints depending upon desired temporal performance.

In the preferred embodiment of the present invention, the computer planning system 35 provides ability to interpolate between "checkpoints". Some treatment planning systems provide a means for saving or temporarily storing a plurality of iterations of a treatment plan in the form of an updated version, for subsequent comparison and to permit backtracking. The user is provided a real-time control permitting the user to establish any two plans ("checkpoints") as the end points on a single continuum, thus providing the user an enhanced speed and freedom in exploring various contingent possibilities. Referring to FIG. 3, the GUI display 150 can include a button 158, drop-down menu (not shown), or a similar device which permits access to the list of plans, and a button 158', drop-down menu (not shown), or a similar device which permits adding the current plan to the list. The interpolate between checkpoints function can allow the user to make some changes, save the modified plan as another version, and then later recall any of the prior versions in order to basically slide back and forth within the continuum between those versions, or prior versions, or with the current display plan, to further develop even more contingent versions.

Conceptually, the interpolate between checkpoints function is a multiple level undo, which can functionally utilize linear interpolation between dose values of evaluation/optimization sampled points. This function, however, is not limited to the comparison of only prior versions of a plan created using the tools of this system. Interpolation between two checkpoints can be accomplished by first determining a value of radiation dose at each of a corresponding set of points representing a radiation dose distribution for the first and the second checkpoints created on different platforms. Note that although other methodologies are within the scope of the present invention, this function is preferably implemented using linear interpolation applied between the values of radiation dose for the sets of points representing the radiation does distributions for the first and the second checkpoints.

The plan optimization software 36 can convert the intermediate (or final) proposed radiation treatment plan into a deliverable discrete radiation treatment plan through discretization of the radiation beam intensities, forming the radiation beam arrangement into corresponding radiation beam intensity settings compatible with a preselected delivery device 39, such as, for example, conformal radiation therapy delivery device. The software 36 can then automatically graphically display to the user the deliverable discrete radiation treatment plan. This can be accomplished by providing an optimization objective function constrained by the value of radiation dose at each point in the radiation dose distribution or at a sampled set thereof representing the radiation dose distribution.

In order to permit the real-time interactive plan adjustments referenced above on current generation computer hardware, the objective function, which the computer that processes the respective optimization algorithm frequently optimizes, can be defined or restated such that it is compatible with rapid (temporal) optimization, without significant reductions in capability. In the preferred embodiment of the present invention, the computer planning apparatus 35 can provide optimization with monotonic first derivatives of objective contributors. The computer planning apparatus 35 can provide an algorithm that reformulates the goals such that each contributor to the objective function is monotonic in its first derivative in order to achieve a significant decrease in the time required to perform the optimization. By focusing attention on the objective function the computer must frequently optimize, rather than each objective function optimized, a significant reduction in computational time can be achieved with minimal computational effort. Note, applying the algorithm to all objective functions optimized is nevertheless within the scope of the present invention.

Plan evaluation point selection is another methodology that provides temporal optimization. Selecting sample points for evaluation of the various iterations of a radiation treatment plan can significantly increase temporal performance. This sampling can be either completely random or random but with a bias to increase sampled probability adjacent regions of particular relevance. In the preferred embodiment of the present invention, the computer planning apparatus 35 provides an algorithm for automatic selection of minimal plan evaluation points to enhance speed and interactivity by identifying a smaller than typical number of plan evaluation points within the patient at which to simulate the treatment dose. These plan evaluation points are distributed sufficiently such that the software 36 is "aware" of the important dose features. As performance is inversely proportional to the number of such plan evaluation points, the algorithm can identify the smallest possible group that meets that criterion, the trade-off being the number of plan evaluation points both constrain the performance and dictate accuracy.

For example, one might have 1,000 different parts of the tumor that dose is calculated for used to calculate the objective function, and there may be 50,000 other points spread out throughout the patient. If the algorithm selected the 50,000 points, it would provide a very accurate description of the treatment plan, but the calculations would take an unacceptable amount of time. If the algorithm only selected 5 points, the result would be a very inaccurate description of the treatment plan. If the algorithm, however, selected 500 points, the accuracy would depend upon where those points are strategically located. Therefore, the respective algorithm can select the smallest possible number of points in the proper position, so as to have a minimum number of points that still sufficiently define the dose delivered to the patient.

A plurality of target tumor volume sampled points and a plurality of structure volume sampled points can be obtained by randomly sampling a radiation dose distribution or beam arrangement of a precedent radiation treatment plan, as described previously. This radiation treatment plan can be either an imported plan or a prior iteration of a proposed radiation treatment plan. The plan optimization software 36 determines a value of radiation dose at each of the target tumor volume sampled points and the structure volume sampled points. An optimization objective function can then be constructed or modified by adding a term to the objective function for each of the of target tumor volume sampled points and each of the structure volume sampled points. Each term provides an extremum (a minimum or maximum constraint) to the objective function, which corresponds to the radiation beam arrangement of the precedent radiation treatment plan.

Note that to ensure integrity of a radiation treatment plan developed using sample points rather than the entire radiation does distribution, the software 36 can separately provide random sampled points to be utilized for plan evaluation that are separate and distinct from those utilized for plan optimization. That is, the software 36 can construct an objective function constrained by the value of radiation dose at each of a plurality of plan optimization sampled points that is distinct from that utilized for plan evaluation. Thus, the user is evaluating the proposed treatment plan rather than merely evaluating the mathematical model utilized by the software 36.

Temporal efficiency can further be increased through use of selective recalculation. For example, to perform an evaluation of an iteration of a proposed radiation treatment plan, the user is generally provided a two-dimensional image slice, such as, for example, the image 161, illustrated in FIG. 3. Thus, the software 36 need only recalculate the value of radiation dose for the plan evaluation sampled points associated with the image 161 currently displayed, rather than recalculate values for the radiation dose of the each plan evaluation sampled point for each image slice, including those not currently displayed.

Temporal efficiency can still further be increased through use of conjugate gradient algorithms to determine and display radiation dose minimum and maximum values for each target or structure. For example, the software 36 can identify for each of the target tumor volume and non-target structure volume, a small set of the sampled points having the highest radiation dose values (e.g. 5 sampled points) and a small set of the sampled points having the lowest radiation dose values. The software 36 can apply a gradient assent algorithm to each small set having the highest radiation does values to determine and to display (FIG. 10) the radiation dose maximum 166 for the target tumor volume and non-target structure volumes. Correspondingly, the software 36 can apply a gradient descent algorithm to the small set having the lowest radiation dose values to determine and to display the radiation dose minimum 167 for the target tumor volume and the non-target structure volumes. Utilizing a small set of sampled points rather all sampled points, or the entire radiation dose distribution, significantly reduces the time required to calculate the minimum and maximum radiation dose values for the target and structures.

In an embodiment of the present invention, the algorithm can also conduct two different sets of plan evaluation samplings: The first set coincides with the points that are evaluated in the objected function, i.e., the ones that contribute to the feedback. The second set coincides with the points used to formulate the DVH curves and other statistics. The algorithm evaluates the objective function more frequently than the algorithm calculates the DVH curves and other statistics. The algorithm can, therefore, afford to use more points for that latter group. Thus, the algorithm attains temporal efficiency by using a smaller subset of points when it needs to recalculate the objective function.

A Fast IMRT Delivery Efficiency Improvement slide control 156 or other suitable tool (FIG. 3) can be added to provide an additional constraint, which may be utilized to constrain the solutions by adding an additional cost contributor which can dominate optimization process, and thereby minimize the effects of the other contributors. That is, a constraint proportional to the number of radiation bean field segments and a constraint proportional to average radiation beam attenuation (for intensity modulated radiation therapy systems) can be added to the objective function as a methodology of controlling efficiency of the radiation treatment plan. This combination of constraints enables the user to control the tradeoff between dosimetric quality (how well the plan meets clinical goals related to dose distribution) and delivery efficiency (delivery speed).

For example, in the preferred embodiment of the present invention, if dosimetric cost (cost associated with the quality of the dose distribution) is below a maximum acceptable level, the total cost does not include the component of the delivery cost, e.g. Total Cost=Dosimetric Cost. If however, the dosimetric cost is above the maximum acceptable level, total cost can be constrained by delivery cost, e.g.

Total Cost=Dosimetric Cost+$LS$*(Delivery Cost−Acceptable Level);

where LS is a large positive number, and Delivery Cost is related to temporal efficiency of delivery. If the complexity for the delivery device 39 is based on the total monitor units rather than the total segment count (as is the case for MIMiC), Delivery Cost can be defined as follows:

$$\text{DeliveryCost} = \frac{\sum_{b=0}^{\text{NumPencilBeams}-1} (1 - \text{RelativeIntensity}[b])}{\text{NumPencilBeams}};$$

where NumPencilBeams is the number of pencil beams that hit the target tumor volume, and RelativeIntensity ranges from 0 to 1 where 1 represents full transmission. For efficient plans, the collimator leaves are open for the majority of the time. For inefficient plans, RelativeIntensity is near 0.

With reference again to FIGS. 2A, 2B, and 2C, the next step in the planning system 30 is often described as an Instrument Fitting Step 108. The resulting optimized set of radiation beam positions and beam weights, or beam intensities for the radiation beam segments, is fitted into the delivery capabilities of, the delivery device 39. In other words, upon completion of fine tuning of the treatment plan, using the various slide controls, such as slide control 154, and dragging the isodose contours 162 using screen pointer 163, etc., the next major step is to make appropriate conversions unique to the type of delivery device 39 selected, and deliver the tailored radiation treatment plan to the selected delivery device 39 for treating the patient. Note, although shown as a separate step, in the preferred embodiment of the present invention, the Instrument Fitting Step 108 is preferably functionally combined with the Plan Optimization Step 107.

The software 36 provides a number of different outputs, depending upon the device 39 selected. The computer planning apparatus 35 can provide a number of additional other data and graphs which allow the user to verify the results and allow the user to "test fire" the radiation treatment plan, delivering the planned dose to test equipment 37. This advantageously provides the user the ability to ensure that the treatment plan results match what the computer planning apparatus 35 and user expect them to be. In the preferred embodiment of the present invention, the GUI display 150 can include a button (not shown), drop-down menu (not shown), or a similar device, which permits the user to approve the radiation treatment plan. Note, typically the user must respond to a security protocol, e.g. enters a password, to complete the approval of the radiation treatment plan. The computer planning apparatus 35 can then automatically make a connection via area network 33 to the selected delivery device 39, and delivers the particular radiation treatment plan associated with a particular patient. In its most basic form, the radiation treatment plan in this stage of development commands the delivery device 39 as to how much and what duration radiation is to be delivered from a plurality of different directions.

The developed plan may or may not always be compatible with the selected delivery device 39. The various plan delivery mechanisms of the various delivery devices 39 often require that beam fluences take on specific discrete values, whereas the optimizers of the various embodiments may work in either discrete or continuous space. For embodiments where plan optimization is developed in continuous space, various methodologies, such as, for example, "mode fold" discretization and "inferred valley" discretization, or other discretization methodologies known to those skilled in the art, can be used separately or in combination as a mechanism for converting such optimized plans into deliverable discrete ones. For example, to simplify and/or accelerate the delivery of intensity modulated treatment fields through a typical multi-leaf collimator, a limited number of discrete intensity levels are often used in determining the optimal treatment fluence map. Many systems currently provide for simple sets of these levels (e.g., 0-100%, in 10% steps). The actual levels used, however, can have a dramatic effect on both treatment simplicity and speed. Likewise, the optimal levels for one treatment plan are typically different than those for another.

In an embodiment of the present invention, the computer planning apparatus 35 can also provide an optimization objective function that can be utilized to develop an optimized radiation treatment plan having a fixed set of discrete radiation beam intensity values, from a precedent radiation treatment plan characterized by having arbitrary radiation beam intensity values. The objective function can iteratively evaluate a precedent radiation treatment plan and a plurality of subsequent radiation treatment plans derived from the precedent radiation treatment plan, to determine a combination of discrete radiation beam intensities. From this determination, the software 36 of the computer planning apparatus 35 can provide an optimized radiation treatment plan having clinical attributes substantially matching the clinical radiation delivery goals of the precedent radiation treatment plan. The computer planning apparatus 35 can maintain a record of multiple radiation treatment plans, which can be evaluated by the optimization objective function. The optimization objective function is constructed such that it can infer the combination of discrete radiation beam intensities required to substantially match the clinical radiation delivery goals of a precedent radiation treatment plan from the radiation treatment plans evaluated.

In another embodiment of the present invention the computer planning apparatus 35 includes the "mode fold" discretization algorithm to provide for rapid estimates of the ideal fluence levels for a given treatment field. The algorithm identifies the optimal levels for fluence discretization by identifying those in the fluence probability distribution. In an embodiment, the algorithm performs under an assumption that the discrete levels should be decomposable into combinations of a subset of those levels, such that N levels are achieved using combinations of $\log_2 N$ levels. The algorithm works by selecting notable modes from a probability distribution inferred from the fluence data at various resolutions. A probability estimator works by expanding a window of samples, progressively smoothing the estimated distribution until there are fewer modes than a predetermined constant. These modes are assessed in terms of how well fluences are covered (the size of the mode) and their correlation with its folded distribution (higher if modes will be reinforced by folding, lower if they will be spread out).

In an embodiment of the present invention, the computer planning apparatus 35 can also provide an algorithm that utilizes "inferred valley" discretization. Where the discrete intensity levels are predefined, the computer planning apparatus 35 can include an algorithm that provides a heuristic technique, which adjusts the distance from the optimum to a close-by discrete point based upon inferred gradients. The software 36 can provide a direction vector, which summarizes the approach to the optimum. In an embodiment where the software 36 utilizes a conjugate gradient approach, the direction vector should be the last direction traveled. Where the software 36 utilizes a downhill method, the direction vector should be from a recent trial point to the final optimum point. For inferred valley discretization, a statistically-based assumption is that this direction is along a shallow valley in the objective function, and is therefore a direction of minimal gradient. Preferably, the cost at a point P is modeled as:

$$C_P = C_O + \|P-O\|(a + [b-a]\|[\hat{G} \times (P-O)/\|P-O\|]\|);$$

where: $C_P$=Objective function evaluated at point P; $C_O$=Lowest cost; O=Optimum point in continuous space; and $\hat{G}$=Gradient unit vector from optimizer; a=Gradient along the G vector; and b=Gradient along an orthogonal vector; and wherein the "a" and "b" gradients are calculated by evaluating two trial points and solving.

This function models the cost as being the optimal cost, plus the magnitude of the distance from the current point to the optimal point, times the sum of a vector, plus the difference between the a and b vectors, scaled by a term which is the gradient unit vector's cross product with the line from the current point to the optimal point, divided by the magnitude of the line from the current point to the optimal point. These point costs can be saved for comparison with the final algorithm nomination, therefore, selection of good initial candidate points improve performance. The algorithm can use the closest discrete point, and a point with at least ¼, but no more than ¾, of the dimensions flipped to the second closest discrete levels, wherein the flipped dimensions are chosen based on the distance the point must move to flip.

Referring again to FIGS. 2A, 2B, and 2C, the next step is the Dose Simulation Step 109. This step is functionally the same step as step 105 except it is performed either during or after plan optimization using the optimization engine of the computer planning apparatus 35 of the present invention. The radiation dose to the patient is simulated based upon the control information for the delivery device 39. The computer planning apparatus 35 provides a multitude of outputs both to the delivery device 39 and the user. A "human" needs to check all the results, therefore, as stated previously, the computer planning apparatus 35 can provide additional graphs and data that lets the user "test fire" the treatment plan without the patient and to make measurements of the dose delivered to test equipment 37 to determine if the computer optimized radiation treatment plan coincides with the expectations of the user, and to ensure that the output output of the delivery device 39 matches the radiation treatment plan.

Referring to the decision box in FIGS. 2A, 2B, and 2C, identified as Decision Step 110, the user determines whether the computer optimized radiation treatment plan meets expectations. If so, the user moves on to Output Process and Delivery Step 111. If the plan or results are determined to be unacceptable, undesirable, or even merely subject to improvement, the user returns (loops back) to steps 107-109 and performs the Plan Optimization Step 107 regarding to additional modifications, examination, or analysis, editing dose prescription or moving isodose contours 162; the Instrument Fitting Step 108 regarding computer optimization of beams, and again the Dose Simulation Step 109 regarding performing simulation for review. This loop can be continued until the user determines the plan to be acceptable.

The Output Process and Delivery Step 111 permits the physician to review the simulated radiation dose information and to approve the radiation plan for final patient delivery. After such review and approval, the data to control the delivery device for the specific radiation delivery case is saved to a computer readable medium, or is directly and/or indirectly transferred via area network 33. The data sent is identified as the treatment plan for a particular patient, whereby the plan supplies how much radiation to deliver and from which directions. The data can also include instructions for the timing and movement of members in, for example, a multi-leaf collimator associated with the delivery device 39, radiation source setup information, and conventional patient information. In the preferred embodiment of the present invention, the user need only "click" on a button or a menu item from a drop-down menu to launch an associated algorithm. In the typical situation, a physician or technician will approve the radiation treatment plan and enter a password, which in turn will automatically cause the establishment of a network connection to the delivery device 39.

As previously described, FIG. 2A illustrates a procedure for creating a radiation treatment plan utilizing a computer planning apparatus 35 of the present invention, whereby the apparatus operates in two modes, the first being shown in FIG. 2B "Plan Tweak" mode, and a second "Stand-Alone" mode shown in FIG. 2C, which utilizes a subset of the steps noted above. Referring to FIG. 2C, the "Stand-Alone" mode comprises steps 99-101, acquiring the tumor image and establishing initial beam positions, then skips steps 102-106 which are generally necessary only to the conversion of a prior system plan, such as, for example, the CORVUS® planning system, into a representation of that plan in the computer planning apparatus 35 of the present invention, and then jumps directly to step 107 for plan optimization, step 108 instrument fitting beam optimization, step 109 dose simulation for review, step 110 iterative loop decision till acceptance of the plan, and finally the Output Processing and Delivery Step 111.

Embodiments of the present invention include a graphical user interface. Referring primarily to FIG. 3, a computer system or apparatus, such as computer planning apparatus 35, can have a graphical user interface (GUI) 150 through which operating system and application software is functionality displayed and accessed. A GUI, such as GUI 150, can represent computer application programs, documents, and data files as graphically displayed GUI objects, such as icons and menus. GUI objects can be manipulated by a user to control and activate system and application functions. A user may manipulate GUI objects by means of a pointing device such as a mouse, touch screen, or other input device (not shown). A mouse is an input device which, when moved over a surface, moves a display screen pointer such as, for example, display screen pointer 163 in a corresponding direction. A mouse typically has a number of buttons which can be pressed ("clicked") to select a GUI object being pointed at by the pointer, and to activate the GUI object's associated function. GUI operating systems and applications may also be referred to as "point-and-click" systems.

GUI objects may include user selectable interfaces such as, for example, drop-down menu 151, checkbox 152, text entry field 153, button 158, and slide control 154 (which can include horizontal or vertical handles or bars 157 that can be dragged with the mouse or other point device causing an update to the GUI object's associated function, upon release). The GUI 150 may also display a GUI object in the form of at least one graphical image of a tumor or tumor slice, such as the scan image 161, displayed in scan window 160. The GUI 150 may also simultaneously display other graphical images such as isodose contours 162 depicting isodose variances relationally plotted with respect to the tumor locus. The GUI 150 may also display at least one GUI object in the form of graphical display tabs in analysis window 170, calculations, or other statistics inputted to or outputted by application software.

As previously stated, the preferred embodiment of the invention displays a plurality of user selectable interfaces such as, for example, drop-down menu 151 and selector button 158; at least one scan window 160, such as a CT scan image 161 with a dose overlay including isodose contour 162; and a "manual tool" in the form of a screen display pointer which can allow a user to outline what the user deems to be tumor material, typically on a slide-by-slide basis. The tool is typically displayed as a mouse-type pointer similar to screen pointer 163. The GUI 150 can also include an automated volume structure selector (not shown), which can allows the user to just "click" on it, whereby it would automatically locate the boundaries of the tumor and automatically make the adjustments where the tumor is very well differentiated. Additionally, the GUI 150 can include user selectable interfaces such as, for example, drop-down menus 151, 151' or checkboxes 152, 152' to select a target or structure; text entry fields 153, 153' (e.g. dose goals, dose limits); slide controls 154, 154', 154", to adjust the importance of various parameters, slide controls 155, 156, to interpolate between plans or adjust software performance; and selection tabs 171 of analysis window 170 which present various statistics.

In an embodiment of the present invention, part of the GUI window display 150 is context dependent. The interface includes at least one drop-down menu 151 with selectable components. For illustrative purposes and referring to FIG. 3, a "target" selection 180 is devoted to the selection of the different healthy tissue organs based upon type of target tissue organ. Selection of a specific target thereof will allow relational entries or adjustments with regard to the specific target. In alternative embodiments, a series of tabs or checkboxes (not shown) may be used instead. The preferred embodiment includes a drop-down menu 151 for "target" selection 180 and a drop-down menu 151' for healthy tissue "structure" selection 181.

For example, if the "target" tumor is due to prostate cancer, typically, healthy tissue "structures" of interest relevant for the treatment plan would include the rectum and the bladder. The user would identify and access the structure selection 181 via the structure's drop-down menu 151 to select each of the healthy organs of interest. The control, in conjunction with a text entry field 153', would provide the ability to adjust the "dose limit" or each to the selected healthy organ, i.e., if the user selected bladder from the list, then that displayed control applies to bladder, if the user selected rectum from the list, that same control applies to rectum.

In an embodiment of the present invention, the GUI 150 also includes selector buttons, such as, for example, selector buttons 158, wherein a single "click" will launch associated algorithms. At least one of the buttons, button 158 relates to checkpointing whereby selection of the button 158 produces an on-screen list showing editable saved plans. Another button 158' typically launches an algorithm to save a plan along with associated constraint parameters. The functions, however, relating to selector buttons 158, 158', can instead be related or assigned to a drop-down menu similar to drop-down menu 151 and vice versa or other GUI methodology of initiating an event.

As stated above, the GUI 150 includes a window 160 displaying a scan, or other image 161. The scan 161 is generally most heavily utilized during the Anatomy Tools Step 101 and Plan Optimization Step 107. The scan 161 provides a two-dimensional representation of a three-dimensional image, either in full or slice-by-slice. The computer planning apparatus 35 of the present invention contains an algorithm, which displays and reflects current or selected plan parameters, such as plan radiation beam intensity, in the form of isodose contours 162. Alternatively, instead of displaying dose on the individual slices using isodose contours 162, the user may select the display to be in the form of transparent color washes, e.g., redder if there is more dose and bluer if there is less dose.

As perhaps best shown in FIGS. 3 and 4, in an embodiment of the present invention, a screen display pointing device 163, typically in the form of a mouse pointer or crosshairs, is responsive to an input device (not shown). This device supports several features described above. In an embodiment, the user can be provided the ability to manipulate a DVH curve 175 as a methodology of inputting dose or structural limitations by "grabbing" the lines or contours on the graph to manipulate their position. In the preferred embodiment of the present invention, the user is also provided the ability to manipulate the isodose contours themselves, such as, for example, isodose contours 162, 162', by use of the pointing device to grab and drag an isodose contour where the user desires the isodose contour to be. Dragging on the image of an isodose contour, such as, for example, isodose contours 162', drags the dose by establishing an absolute constraint along a line 190 between the start dragging point 191 and the stop dragging point 192. When the user releases the "grab" of the pointing device on the isodose contour 162', the action commands an algorithm of software 36 to output a new plan wherein the dragged line 190 forms the added constraint. The pointing device may also be used for more basic GUI functions such as selecting a drop-down menu item 151, "clicking" on a button 158, selecting a checkbox 152, or grabbing a handle 157 of a slide controls 154, 155, or 156. In an alternate embodiment, the GUI 150 provides an on-screen dose indicator to indicate the dose at any given point on the scan window 160. Positioning the pointing device 163 on or adjacent to the isodose contours overlaid on the tomographic scan 161 causes the display of the dose value of a particular point in the tumor structure. Mousing over the image will yield a continuously updated dose measurement. In another embodiment, the on-screen dose value is displayed immediately adjacent to a crosshair curser as it moves. In yet another alternative embodiment, the GUI 150 provides for direct dose drawing whereby the user establishes or identifies targets or structures and constrains them to the selected isodose contour 162. In this embodiment, a separate control (not shown) is typically used to establish dose-drawing mode.

Checkboxes are a simple tool for inputting simple information into a computer system/apparatus. In an embodiment of the present invention, where the desired input into the computer planning apparatus 35 is merely a selectable inclusion of an item into the optimization process, checkboxes 152 may be utilized. For example, a checkbox 152 may be used to select the prostate as a target or the rectum as a healthy tissue structure.

Text entry fields are a simple tool for entering numerical data into a computer system/apparatus algorithm. In an embodiment of the present invention, text entry fields 153 are available for entry of target goal dose and healthy structure dose limit, although other prescription parameters are also possible.

Slider controls are also a simple tool for entering both discrete and non-discrete adjustable parameters into a computer system/apparatus algorithm. In the preferred embodiment of the present invention, slider controls 154, 155, 156, are the preferred methodology for entry of various adjustable parameters. For at least one target, the user would specify the desired dose level in the text entry field 153 corresponding to "goal dose." This may be accomplished by entering a numeral input in the text entry field 153 for each of the at least one targets selected by the drop-down menu 151. For example, the user would input numeral 67.25 in the goal dose field 157 for the prostate. Correspondingly, the GUI 150 displays at least one, but typically two or more slide controls 154, 154" to set limitations for use in the computer's calculation of the radiation treatment plan. Basically, in the preferred configuration, slide controls 154, 154' are provided to constrain the homogeneity and conformality of the selected target, as illustrated in FIG. 3.

For example, for some target tumors the user would wish to constrain the maximum dose level to avoid entering too much dose in the target tumor. In other situations, the user may not be concerned with the level of dose and therefore may allow the computer to enter as much dose as the algorithm decides in order to provide the optimal plan. In other situations, the user may be concerned that all targets get at least X level of dose. In yet others, the user may be concerned that all targets get between X and Y level of dose. Additionally, slide controls such as, for example, slide control 154' are also effective for dictating structure constraints, such as "importance."

Also for example, in using the "Target Homogeneity" slide control 154" of FIG. 3, the user enters a 50 Gy goal dose in the text entry field 153 for a target prostate tumor. The computer planning apparatus 35 then develops and displays a plan that shows 50 Gy everywhere in the tumor. However, due to the shape of the tumor, the plan results in 80 Gy being delivered to some part in the middle of the tumor. The user determines the dose is excessive. The user selects the "Target Homogeneity" slide control 154" which functions as an influence input to the algorithm to not allow "hotspots." The user, with a mouse, pointer, or equivalent, "clicks" on the control "handle" 157 of "Target Homogeneity" slide control 154" and slides the handle 157. In the preferred embodiment, the user would slide the handle 157 to the right. Nothing would happen until the user releases the device (mouse button), and thus the handle 157 is in the new position. The effect of releasing the device (mouse button) results in recalculation and display of a revised or new treatment plan. Running this particular control ever farther effectively limits the variation of the dose within the tumor. If the 80 Gy spot or 80 Gy isodose contour 162 drawn on the screen 160 remains, an additional increase in the slide handle 157 position functionally should result in the 80 Gy spot or isodose contour 162 disappearing from the screen 160.

In an embodiment of the present invention, a slide control 155 is used in conjunction with the "partial undo" function whereby dynamic adjustment is provided for interpolating fluence or dose directly while the adjustment is being made and resolving the interpolating constraint parameters when the control is released. In an embodiment of the present invention, a slide control, similar to the slide control 155, also functions in the above manner when interpolating between "checkpoints" (previously saved radiation treatment plans).

Figure 5A:
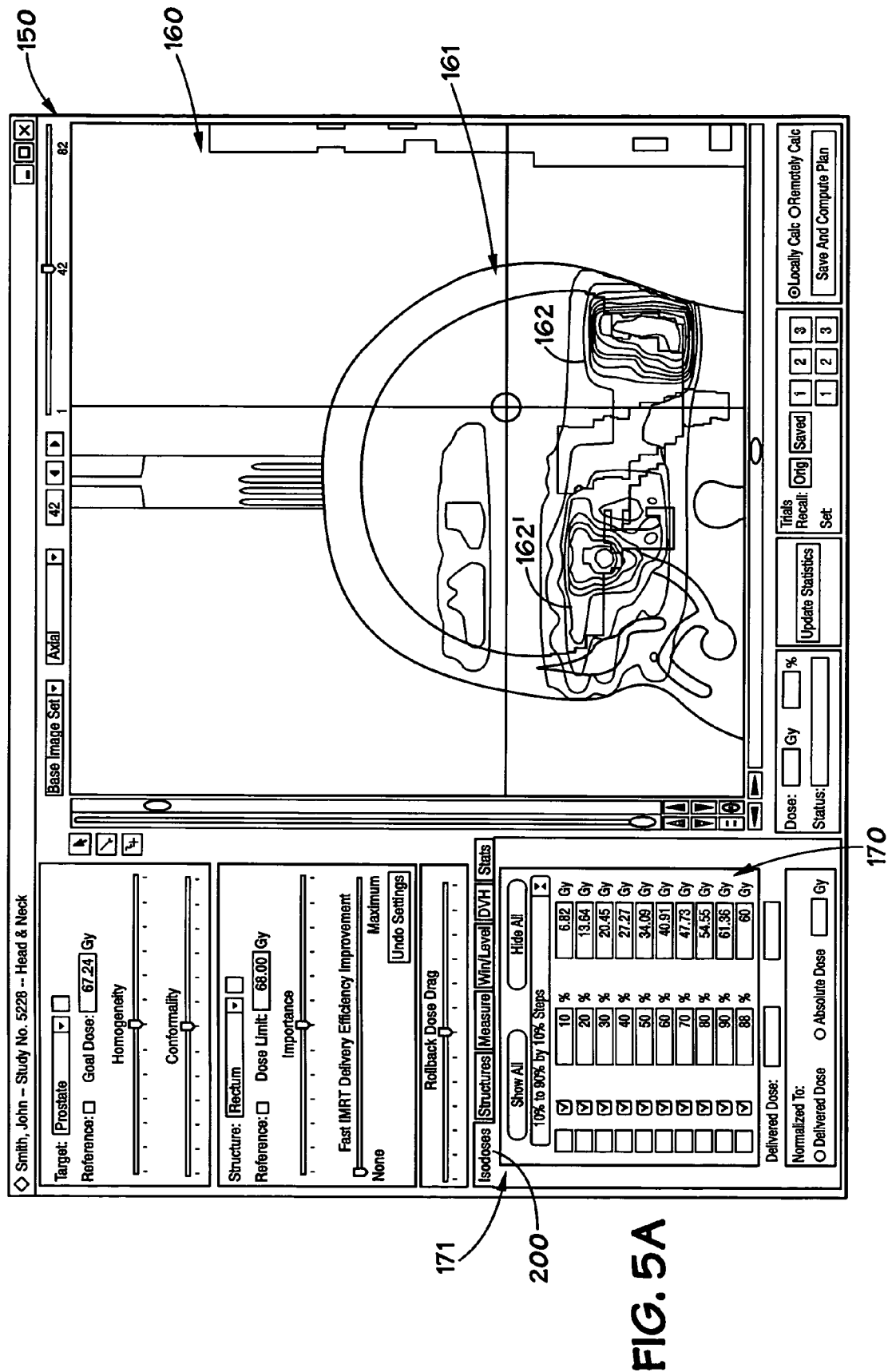
FIG. 5A-G is a plan view of a subset of selectable tabs included within a results window of a graphical user interface according to an embodiment of the present invention.
Figure 5B:
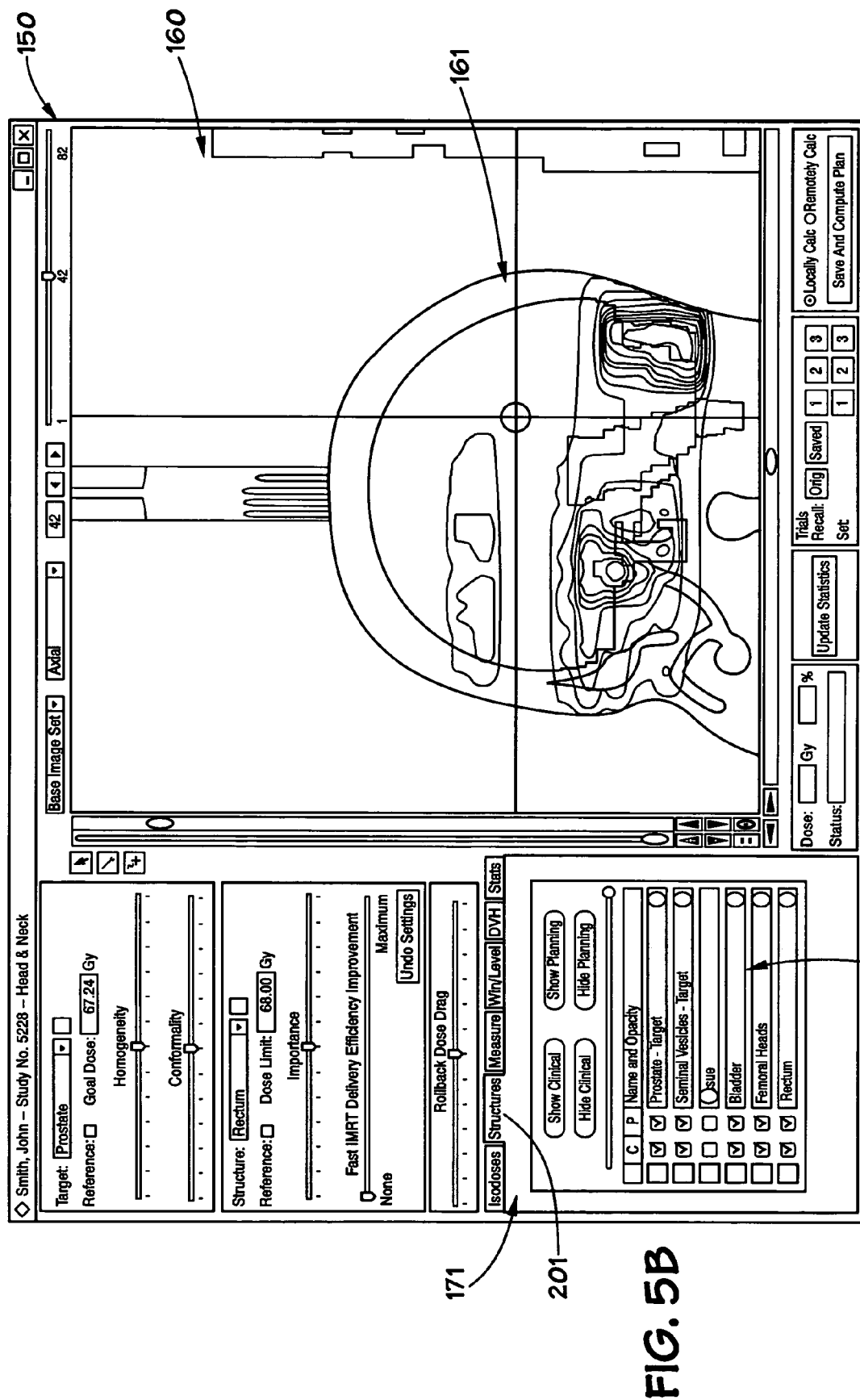
Figure 5C:
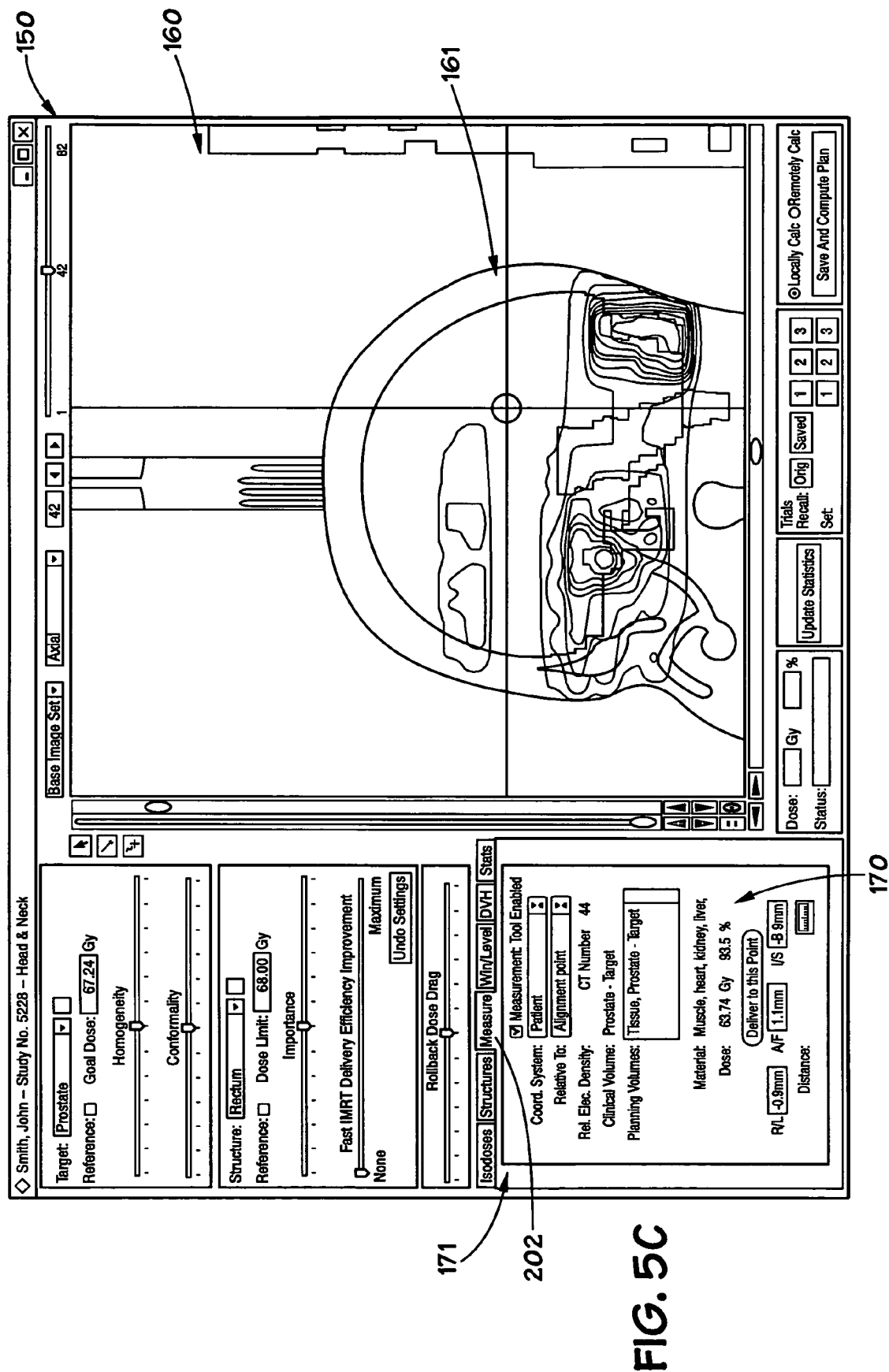
Figure 5D:
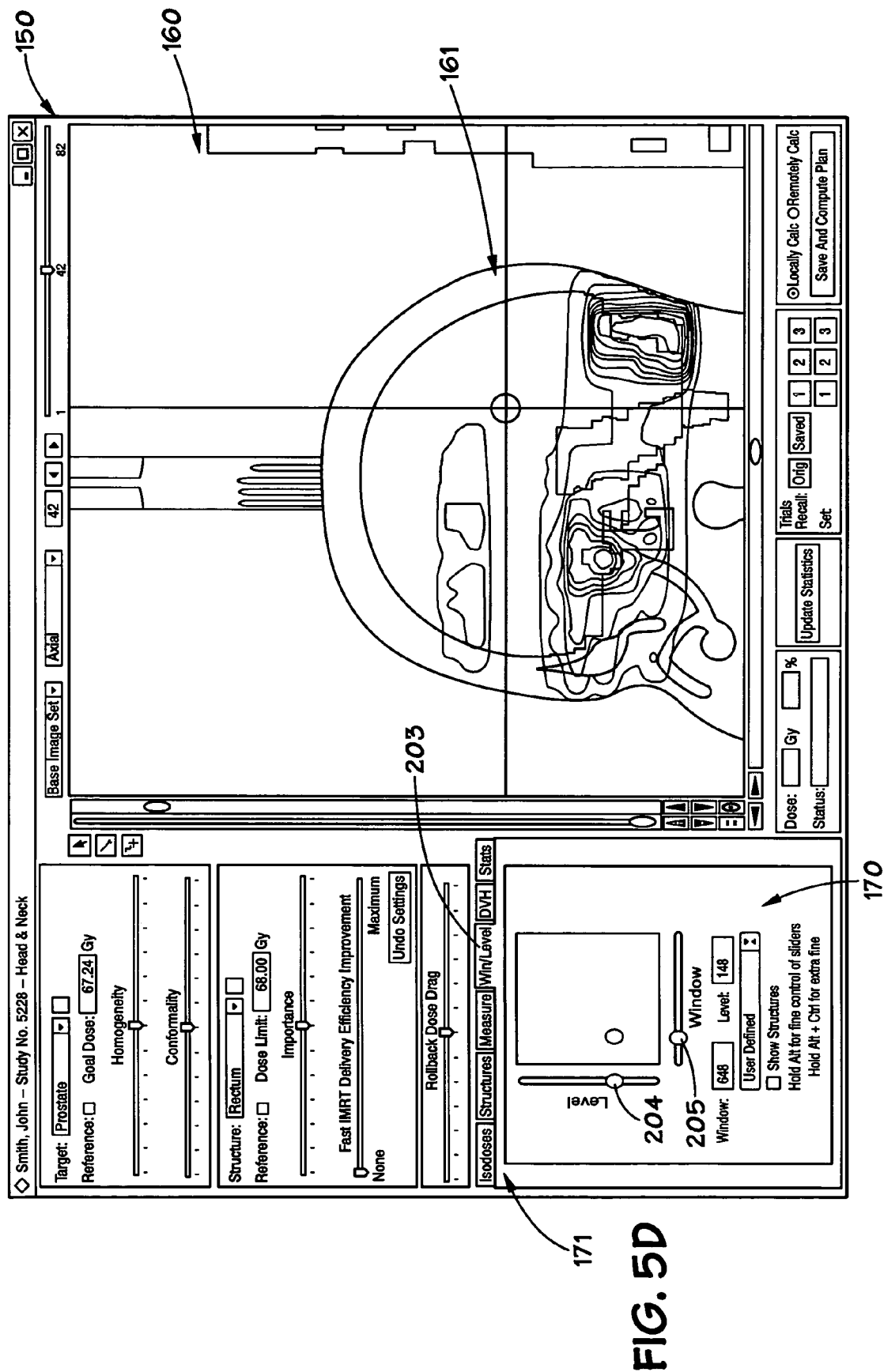
Figure 5E:
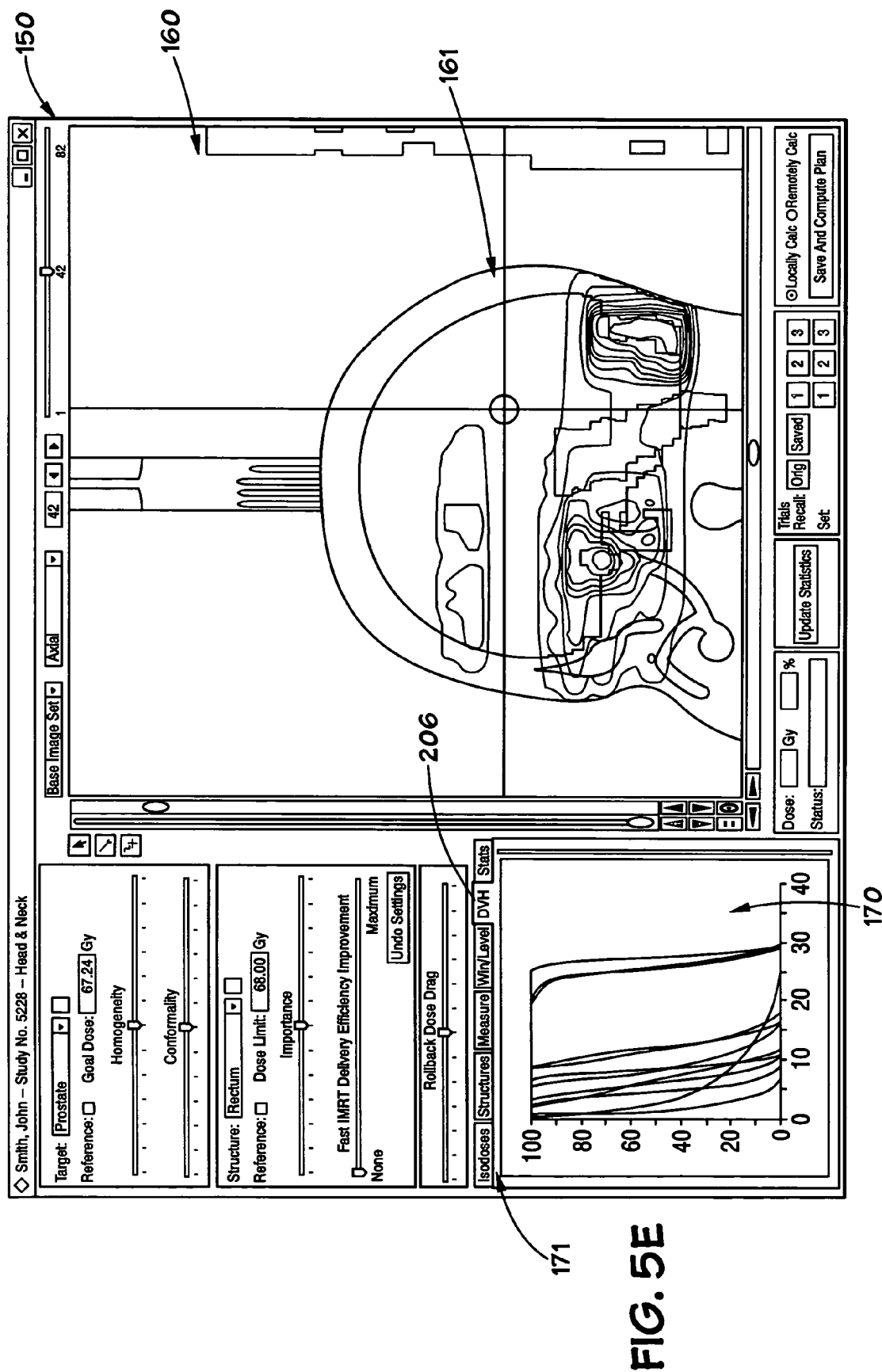
Figure 5F:
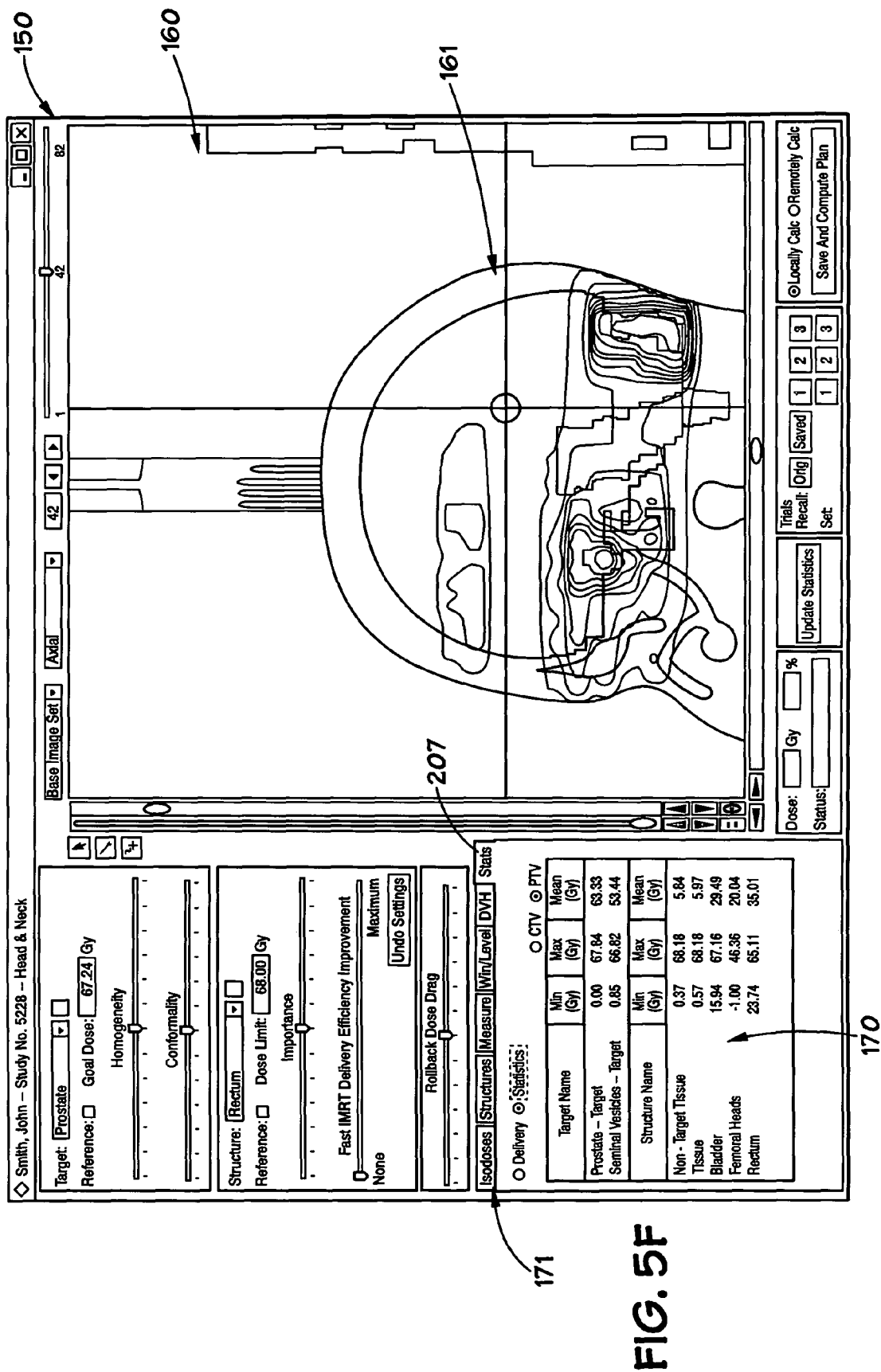
Figure 5G:
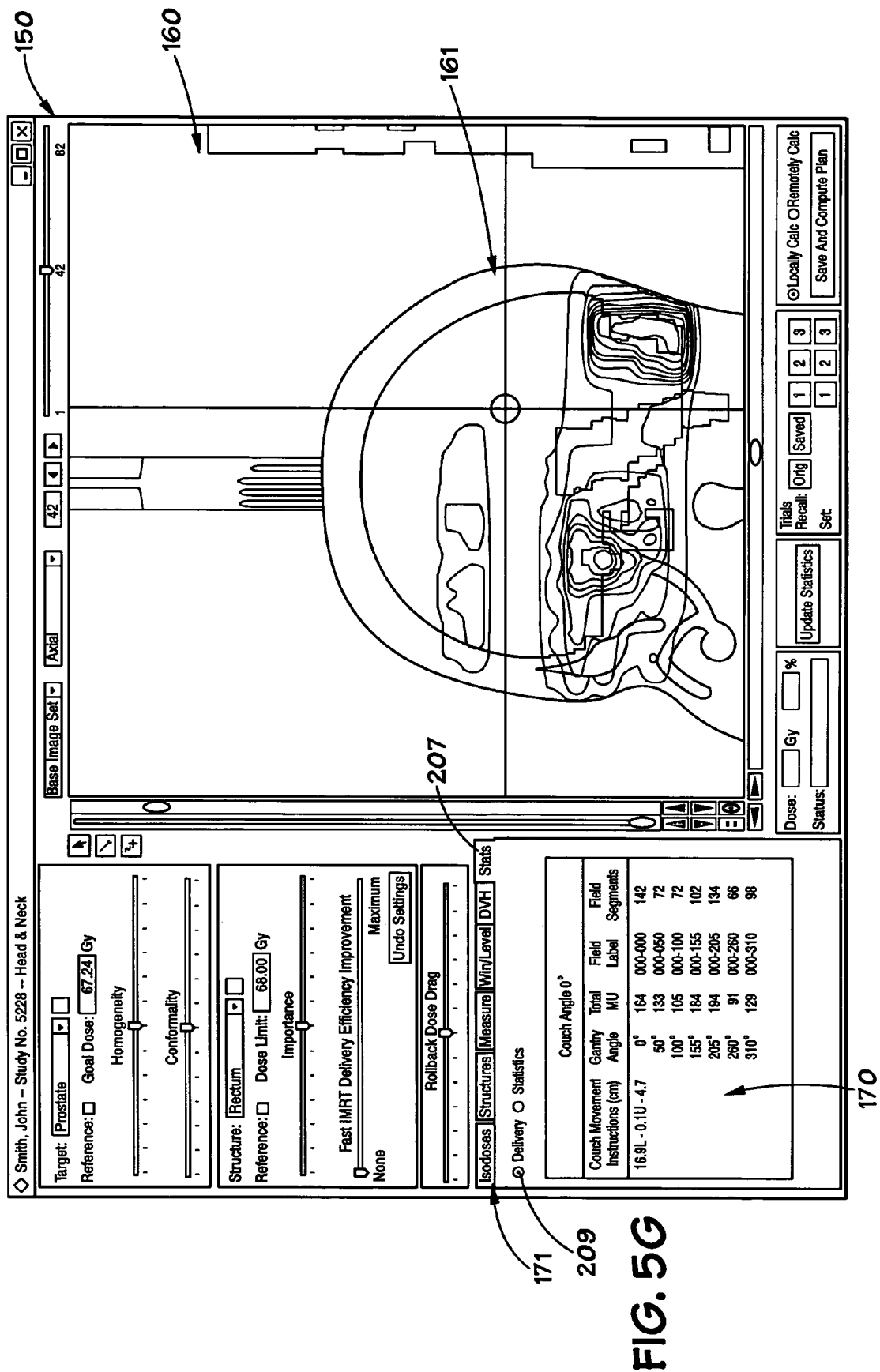

In embodiments of the present invention, a small portion of the screen, analysis window 170, is devoted to the display of selection tabs. Selection tabs 171 (FIGS. 3, 4, and 5A-G) are utilized for the display of various plan optimization outputs utilized by the user in assessing the plan. These tabs include relevant output information such as: Isodoses 200 (FIG. 5A); Structures 201 (FIG. 5B); Measure 202 (FIG. 5C); Win/Level 203 (FIG. 5D); DVH curves 206 (FIG. 5E); and Stats 207 (FIG. 5F-5G). In an alternative embodiment, a small portion of the screen can be devoted to a set of tools performing the functionally equivalent output of tabs 171. Referring to FIG. 5A, the Isodose tab 200 in the analysis window 170 displays the color and dose level of the isodose contours 162 depicted in tomographic type scan 161 of scan window 160 of GUI 150. Referring to FIG. 5B, the Structures tab 201 displays buttons, checkboxes, and display boxes which provide an appearance template for the on-screen structures. Referring to FIG. 5C, the Measure tab 202 provides a tool to sample image values and the dose at a point on the scan 161 of scan window 160 of GUI 150. Referring to FIG. 5D, the WinLevel tab 203 includes controls 204, 205, for image 161 brightness and contrast. Referring to FIG. 5E, the DVH tab 206 displays the various DVHs. Referring to FIG. 5F, the Stats tab 207 displays the actual minimum, maximum and mean doses planned for each structure. Referring to FIG. 5G, the Stats tab 207 also displays a summary of the delivery machine setup showing radiation value and complexity, when the "Delivery" indicator 209 has been selected.

It is important to note that although embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include: nonvolatile, hard-coded type media such as read only memories (ROMs) or erasable, electrically programmable read only memories (EEPROMs), recordable type media such as floppy disks, hard disk drives and CD-ROMs, and transmission type media such as digital and analog communication links.

In the drawings and specification, there have been disclosed a typical preferred embodiment of the invention along with some alternative embodiments, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification. For example, although transmission of data between the various components as the system 30 is accomplished over an area network 33, the data can be easily "hand-carried" or delivered by other means. Also for example, the various components of the GUI are interchangeable, e.g. checkboxes are substitutable with drop-down menus, and vice versa.

The invention claimed is:

1. A system to determine an optimal radiation beam arrangement for applying radiation to a tumor target volume while minimizing radiation of a non-target structure volume in a patient, the system comprising a computer planning apparatus including:

a treatment plan optimization computer having a memory to store data and treatment plan optimization software therein; and an input device in communication with the treatment plan optimization computer to provide user access to control functions of the treatment plan optimization software;

the treatment plan optimization software comprising a set of instructions that, when executed by the treatment plan optimization computer, causes the computer to perform operations to computationally obtain a proposed radiation beam arrangement and to computationally iteratively optimize the proposed radiation beam arrangement based on a plurality of constraints to form the optimized radiation beam arrangement, the treatment plan optimization software including a graphical user interface to display an at least two-dimensional image slice of the tumor target volume and the non-target structure volume, graphical objects, and graphical representations of radiation dose distribution calculated for each iteration of the proposed radiation beam arrangement overlaid upon the displayed image slice, the operations comprising:

receiving inputs from the input device representing direct graphical user manipulation of a graphical representation of radiation dose distribution for a current iteration of the proposed radiation beam arrangement displayed on the graphical user interface, and responsive to user manipulation of the displayed graphical representation of radiation dose distribution for the current iteration of the proposed radiation beam arrangement, computationally obtaining and providing data to graphically display a graphical representation of radiation dose distribution for a next iteration of the proposed radiation beam arrangement which substantially realizes the graphically altered radiation dose distribution, to thereby iteratively form the optimized radiation beam arrangement;

the graphical representation of the radiation dose distribution for the current iteration of the proposed radiation beam arrangement displayed on the graphical user interface and directly graphically manipulated via the input device, comprising one or more of the following:

an isodose plot including a plurality of isodose contours according to the current proposed radiation beam arrangement overlaid upon the image slice of the target tumor volume and the non-target structure volume, at least one of the plurality of isodose contours of the isodose plot directly graphically manipulatable by a user to graphically alter proposed radiation dose to at least one volume of interest to produce the next iteration of the proposed radiation beam arrangement which substantially realizes the graphically altered radiation dose, the at least one volume of interest comprising one or more of the following: the target tumor volume and the non-target structure volume, and a plurality of dose volume histogram curves according to the current proposed radiation beam arrangement, at least one dose volume histogram curve of the plurality of this volume histogram curves directly graphically manipulatable by the user to graphically alter proposed radiation dose to the at least one volume of interest to produce the next radiation beam arrangement which substantially realizes the graphically altered radiation dose.

2. The system as defined in claim 1, wherein the graphical representation of radiation dose distribution for the current iteration of the proposed radiation beam arrangement is in the form of the isodose plot including the plurality of isodose contours; and wherein each isodose contour of the plurality of isodose contours of the isodose plot is directly graphically manipulatable by the user via manipulation of the input device to graphically interface with the respective isodose contour to graphically alter the respective isodose contour to thereby correspondingly alter radiation dose to the at least one volume of interest to produce the optimized radiation beam arrangement.

3. The system as defined in claim 1, wherein the graphical representation of radiation dose distribution for the current iteration of the proposed radiation beam arrangement is in the form of the plurality of dose volume histogram curves; and wherein each dose volume histogram curve of the plurality of dose volume histogram curves is directly graphically manipulatable by the user via manipulation of the input device to graphically interface with the respective dose volume histogram curve to graphically alter the respective dose volume histogram curve to thereby correspondingly alter radiation dose to the at least one volume of interest to produce the optimized radiation beam arrangement.

4. A non-transitory computer readable medium comprising a computer program stored thereon to determine an optimized radiation beam arrangement for applying radiation to a target tumor volume while minimizing radiation to a non-target structure volume in a patient, the computer program comprising a set of instructions that, when executed by a computer, causes the computer to perform the following operations:

providing data to graphically display an image slice of the target tumor volume and the non-target structure volume;

providing data to graphically display radiation dose for the target tumor volume and for the non-target structure volume on the image slice and in a form of a first isodose plot including a plurality of isodose contours according to a first radiation beam arrangement, the plurality of isodose contours of the first isodose plot being directly graphically manipulatable by a user to graphically alter the radiation dose to at least one volume of interest to produce a second radiation beam arrangement which substantially realizes the graphically altered radiation dose, the at least one volume of interest comprising one or more of the following: the target tumor volume and the non-target structure volume;

receiving inputs representing direct graphical user manipulation of a graphically displayed user-selected isodose contour of the plurality of isodose contours of the first isodose plot according to the first radiation beam arrangement; and responsive to the direct graphical user manipulation of the graphically displayed user-selected isodose contour, computationally obtaining, and providing data to graphically display, radiation dose for the target tumor volume and the non-target structure volume on the image slice in a form of a second isodose plot including a plurality of isodose contours according to the second radiation beam arrangement.

5. The non-transitory computer readable medium as defined in claim 4, wherein the computer program further comprises instructions that, when executed by the computer, causes the computer to perform the following operations:
interfacing with a pointing device to graphically alter the graphically displayed user-selected isodose contour of the plurality of isodose contours of the first isodose plot according to the first radiation beam arrangement; and
responsive to a user input to the pointing device, establishing a constraint along a user selected line connecting a start-drag point having a desired level of dose associated with the user-selected isodose contour and an end-drag point having an undesirable level of dose, and setting the level of dose at the end-drag point substantially equal to the desired level of dose, to thereby form the second radiation beam arrangement.

6. The non-transitory computer readable medium of claim 5,
wherein the constraint established along the user selected line constrains dose along the user selected line between the start-drag point and the end-drag point to a value level not to exceed the desired level of dose when the undesirable level of dose is greater than the desired level of dose; and
wherein the constraint established along the user selected line constrains dose along the user selected line to a value level not below the desired level of dose when the undesirable level of dose is less than the desired level of dose.

7. The non-transitory computer readable medium as defined in claim 4, wherein the computer program further comprises instructions that, when executed by the computer, causes the computer to perform the following operations:
interfacing with a pointing device to graphically alter the graphically displayed user-selected isodose contour of the plurality of isodose contours of the first isodose plot according to the first radiation beam arrangement;
responsive to a user input to the pointing device, selecting a portion of the user-selected isodose contour having a user desired level of dose; and
responsive to the user dragging the selected portion of the user-selected isodose contour with the pointing device along a user desired path from a first selected position on the image slice to a second selected position on the image slice, relocating the isodose contour substantially adjacent the user desired path, to thereby form the second radiation beam arrangement.

8. The non-transitory computer readable medium as defined in claim 4, wherein the computer program further comprises instructions that, when executed by the computer, causes the computer to perform the following operations:
interfacing with a pointing device to graphically alter the graphically displayed user-selected isodose contour of the plurality of isodose contours of the first isodose plot according to the first radiation beam arrangement; and
responsive to a user selection of the user-selected isodose contour according to the first radiation beam arrangement, setting a value of radiation dose within the user-selected isodose contour substantially equal to a value of radiation dose outside the isodose contour, to thereby form the second radiation beam arrangement.

9. The non-transitory computer readable medium of claim 4, wherein the computer program further comprises instructions that, when executed by the computer, causes the computer to perform the following operations:
interfacing with a user controlled input device to receive one or more of the following: a minimum radiation dose and a maximum radiation dose, for one or more of the following: the target tumor volume and the non-target structure volume, to define an extremum value input; and
responsive to the extremum value input, constraining isodose contour manipulation of the user-selected isodose contour by the user to prevent an undesirable collateral dose variation.

10. The non-transitory computer readable medium as defined in claim 4, wherein the computer program further comprises instructions that, when executed by the computer, causes the computer to perform the following operations:
interfacing with a user controlled input device to receive a user desired balance between maintaining dosimetric quality and maintaining radiation delivery efficiency for a radiation delivery device, to define an efficiency threshold; and
responsive to the efficiency threshold, constraining isodose contour manipulation of the user-selected isodose contour by the user to maintain radiation delivery efficiency above the efficiency threshold.

11. A non-transitory computer readable medium comprising a computer program stored thereon to determine an optimized radiation beam arrangement for applying radiation to a target tumor volume while minimizing radiation to a non-target structure volume in a patient, the computer program comprising a set of instructions that, when executed by a computer, causes the computer to perform the following operations:
providing data to graphically display radiation dose for the target tumor volume and the non-target structure volume in the form of a first plurality of dose volume histogram curves according to a first radiation beam arrangement, the plurality of dose volume histogram curves being directly graphically manipulatable by a user to graphically alter radiation dose to at least one volume of interest to produce a second radiation beam arrangement which substantially realizes the graphically altered radiation dose, the at least one volume of interest comprising one or more of the following: the target tumor volume and the non-target structure volume;
receiving inputs representing direct graphical user manipulation of a graphically displayed user-selected dose volume histogram curve of the plurality of dose volume histogram curves according to the first radiation beam arrangement; and
responsive to the direct graphical user manipulation of the graphically displayed user-selected dose volume histogram curve, computationally obtaining, and providing data to graphically display, radiation dose for the target tumor volume and the non-target structure volume in the form of a second plurality of dose volume histogram curves according to the second radiation beam arrangement.

12. The non-transitory computer readable medium as defined in claim 11, wherein the computer program further comprises instructions that, when executed by the computer, causes the computer to perform the following operations:
interfacing with a pointing device to graphically alter the graphically displayed user-selected dose volume histogram curve of the plurality of dose volume histogram curves according to the first radiation beam arrangement;

responsive to a user input to the pointing device, selecting a portion of the user-selected dose volume histogram curve located at a first selected position and indicating a first percentage of the target tumor volume permitted to receive more than a predetermined dose level of radiation; and responsive to the user dragging the selected portion of the user-selected dose volume histogram curve with the pointing device along a user desired path to a second selected position, altering the respective percentage of target tumor volume permitted to receive more than the predetermined dose level of radiation, to thereby form the second radiation beam arrangement.

13. The non-transitory computer readable medium as defined in claim 11, wherein the computer program further comprises instructions that, when executed by the computer, causes the computer to perform the following operations:

interfacing with a user controlled input device to receive one or more of the following: a minimum radiation dose and a maximum radiation dose, for one or more of the following: the target tumor volume and the non-target structure volume, to define an extremum value input; and responsive to the extremum value input, constraining dose volume histogram curve manipulation of the user-selected dose volume histogram by the user to prevent an undesirable collateral dose variation.

14. The non-transitory computer readable medium as defined in claim 11, wherein the computer program further comprises instructions that, when executed by the computer, causes the computer to perform the following operations:

interfacing with a user controlled input device to receive a user desired balance between radiation dosimetric cost and radiation delivery efficiency for a radiation delivery device, to define an efficiency threshold; and responsive to the efficiency threshold, constraining dose volume histogram curve manipulation of the user-selected dose volume histogram by the user to maintain radiation delivery efficiency above the efficiency threshold.

15. A method of determining an optimized radiation beam arrangement for applying radiation to a target tumor volume while minimizing radiation to a non-target structure volume in a patient, the method comprising the steps of:

graphically displaying an image slice of the target tumor volume and the non-target structure volume;

graphically displaying radiation dose for the target tumor volume and for the non-target structure volume on the image slice and in the form of a first isodose plot including a plurality of isodose contours according to a first radiation beam arrangement defining a first treatment plan; and directly graphically manipulating a graphically displayed user-selected isodose contour of the plurality of isodose contours of the first isodose plot with a pointing device by a user to alter the radiation dose for at least one volume of interest, the at least one volume of interest comprising one or more of the following: the target tumor volume and the non-target structure volume; and displaying a second isodose plot including a plurality of isodose contours according to a second radiation beam arrangement defining a second radiation treatment plan which substantially realizes the corresponding graphically altered radiation dose.

16. The method as defined in claim 15, wherein the step of directly graphically manipulating the graphically displayed user-selected isodose contour comprises the steps of:

graphically selecting with the pointing device a portion of the user-selected isodose contour located at a first selected position and having a desired first level of dose;

graphically dragging the selected portion of the user-selected isodose contour with the pointing device from the first selected position on the image slice to a second selected position on the image slice having an undesirable second level of dose; and responsive to the movement of the selected portion of the user-selected isodose contour from the first selected position to the second selected position, setting the second level of dose for the second selected position substantially equal to the desired first level of dose, to thereby form the second treatment plan.

17. The method as defined in claim 16, further comprising the step of:

establishing a constraint between the first and the second selected positions on the image slice;

wherein the constraint constrains dose directly between the first and the selected positions to a value level not to exceed the desired level of dose when the undesirable level of dose is greater than the desired level of dose; and wherein the constraint constrains dose directly between the first and the selected positions to a value level not below the desired level of dose when the undesirable level of dose is less than the desired level of dose.

18. The method as defined in claim 15, wherein the step of directly graphically manipulating the graphically displayed user-selected isodose contour comprises the steps of:

graphically selecting with the pointing device a portion of the user-selected isodose contour located at a first selected position and having a user desired level of dose;

graphically marking with the pointing device a user desired path from the first selected position on the image slice to a second selected position on the image slice adjacent the separate portion of the isodose contour, substantially encircling a portion of the image slice encircled by the isodose contour; and responsive to the marking of the user desired path, forming the second treatment plan having radiation dose adjacent the user desired path constrained to the user desired level of dose.

19. The method as defined in claim 15, wherein the step of directly graphically manipulating the graphically displayed user-selected isodose contour comprises the steps of:

graphically selecting with the pointing device the user-selected isodose contour according to the first radiation beam arrangement; and responsive to the selection of the user-selected isodose contour, remediating a value of radiation dose within the user-selected isodose contour to a value approximately equal a value of radiation dose outside the user-selected isodose contour, thereby forming the second radiation beam arrangement.

20. A method of determining an optimized radiation beam arrangement for applying radiation to a target tumor volume while minimizing radiation to an non-target structure volume in a patient, the method comprising the steps of:

graphically displaying radiation dose for the target tumor volume and for the non-target structure volume in the form of a plurality of dose volume histogram curves according to a first radiation beam arrangement defining a first treatment plan; and directly graphically manipulating a graphically displayed user-selected dose volume histogram curve of the plurality of dose volume histogram curves with a pointing device by a user to alter the radiation dose for at least one volume of interest, the at least one volume of interest comprising one or more of the following: the target tumor volume and the non-target structure volume; and displaying the user-selected dose volume histogram curve according to a second radiation beam arrangement defining a second treatment plan which substantially realizes the corresponding graphically altered radiation dose.

21. The method as defined in claim 20, wherein the step of directly graphically manipulating the graphically displayed user-selected dose volume histogram curve comprises the steps of:

graphically selecting a portion of the user-selected dose volume histogram curve at a first selected position with the pointing device, the selected portion of the dose volume histogram curve indicating a first percentage of the target tumor volume permitted to receive more than a preselected dose level of radiation;

graphically dragging the selected portion of the user-selected dose volume histogram curve with the pointing device from the first selected position along a user desired path to a second selected position indicating a second percentage of the target tumor volume permitted to receive more than the preselected dose level of radiation; and responsive to the movement of the selected portion of the user-selected dose volume histogram curve from the first selected position to the second selected position, altering the percentage of the target tumor volume permitted to receive more than the predetermined dose level of radiation.

22. The system as defined in claim 1, wherein the direct graphical user manipulation comprises dragging one of the plurality of graphically displayed isodose contours from a portion of the tumor target volume responsive to user input to a graphically displayed screen pointer through the input device.

23. The system as defined in claim 1, wherein the direct graphical user manipulation comprises dragging one of the plurality of graphically displayed isodose contours into a portion of the tumor target volume responsive to user input to a graphically displayed screen pointer through the input device.

24. The system as defined in claim 1, wherein the direct graphical user manipulation comprises dragging one of the plurality of graphically displayed isodose contours from a portion of the non-target structure volume responsive to user input to a graphically displayed screen pointer through the input device.

25. The system as defined in claim 1, wherein the direct graphical user manipulation comprises dragging one of the plurality of graphically displayed isodose contours into a portion of the non-target structure volume responsive to user input to a graphically displayed screen pointer through the input device.

26. The system as defined in claim 1, wherein the direct graphical user manipulation comprises dragging one of the plurality of graphically displayed dose volume histogram curves to reduce a level of excess dose for a given percentage of the tumor target volume responsive to user input to a graphically displayed screen pointer through the input device.

27. The system as defined in claim 1, wherein the direct graphical user manipulation comprises dragging one of the plurality of graphically displayed dose volume histogram curves to increase a level of dose for a given percentage of the tumor target volume responsive to user input to a graphically displayed screen pointer through the input device.

28. The system as defined in claim 1, wherein the direct graphical user manipulation comprises dragging one of the plurality of graphically displayed dose volume histogram curves to reduce a level of excess dose for a given percentage of the non-target structure volume responsive to user input to a graphically displayed screen pointer through the input device.

29. The non-transitory computer readable medium as defined in claim 4, wherein the received inputs representing direct graphical user manipulation of the graphically displayed user-selected isodose contour comprise inputs representing a user, through use of a pointing device, dragging a portion of the user-selected isodose contour from a location within a portion of the tumor target volume.

30. The non-transitory computer readable medium as defined in claim 4, wherein the received inputs representing direct graphical user manipulation of the graphically displayed user-selected isodose contour comprise inputs representing the user, through use of a pointing device, dragging a portion of the user-selected isodose contour into a location within a portion of the tumor target volume.

31. The non-transitory computer readable medium as defined in claim 4, wherein the received inputs representing direct graphical user manipulation of the graphically displayed user-selected isodose contour comprise inputs representing the user, through use of a pointing device, dragging a portion of the user-selected isodose contour from a location within a portion of the non-target structure volume.

32. The non-transitory computer readable medium as defined in claim 4, wherein the received inputs representing direct graphical user manipulation of the graphically displayed user-selected isodose contour comprise inputs representing the user, through use of a pointing device, dragging a portion of the user-selected isodose contour into a location within a portion of the non-target structure volume.

33. The non-transitory computer readable medium as defined in claim 11, wherein the computer program further comprises instructions that, when executed by the computer, causes the computer to perform the following operations:

interfacing with a pointing device to graphically alter the graphically displayed user-selected dose volume histogram curve of the plurality of dose volume histogram curves according to the first radiation beam arrangement;

responsive to a user input to the pointing device, selecting a portion of the user-selected dose volume histogram curve located at a first selected position and indicating a first percentage of the non-target structure volume permitted to receive more than a predetermined dose level of radiation; and responsive to the user dragging the selected portion of the user-selected dose volume histogram curve with the pointing device along a user desired path to a second selected position, altering the respective percentage of non-target structure volume permitted to receive more than the predetermined dose level of radiation, to thereby form the second radiation beam arrangement.

34. The method as defined in claim 15, wherein the step of directly graphically manipulating the graphically displayed user-selected isodose contour comprises the step of:

dragging a portion of the user-selected isodose contour from a location within a portion of the tumor target volume with use of the pointing device.

35. The method as defined in claim 15, wherein the step of directly graphically manipulating the graphically displayed user-selected isodose contour comprises the step of:
dragging a portion of the user-selected isodose contour into a location within a portion of the tumor target volume with use of the pointing device.

36. The method as defined in claim 15, wherein the step of directly graphically manipulating the graphically displayed user-selected isodose contour comprises the step of:
dragging a portion of the user-selected isodose contour from a location within a portion of the non-target structure volume with use of the pointing device.

37. The method as defined in claim 15, wherein the step of directly graphically manipulating the graphically displayed user-selected isodose contour comprises the step of:
dragging a portion of the user-selected isodose contour into a location within a portion of the non-target structure volume with use of the pointing device.

38. The method as defined in claim 20, wherein the step of directly graphically manipulating the graphically displayed user-selected dose volume histogram curve comprises the steps of:
graphically selecting a portion of the user-selected dose volume histogram curve at a first selected position with the pointing device, the selected portion of the dose volume histogram curve indicating a first percentage of the non-target structure volume permitted to receive more than a preselected dose level of radiation;
graphically dragging the selected portion of the user-selected dose volume histogram curve with the pointing device from the first selected position along a user desired path to a second selected position indicating a second percentage of the non-target structure volume permitted to receive more than the preselected dose level of radiation; and
responsive to the movement of the selected portion of the user-selected dose volume histogram curve from the first selected position to the second selected position, altering the percentage of the non-target structure volume permitted to receive more than the predetermined dose level of radiation.

* * * * *